(12) United States Patent
Rainger et al.

(10) Patent No.: US 9,597,368 B2
(45) Date of Patent: Mar. 21, 2017

(54) PEPTIDE AND USES THEREFOR

(71) Applicants: George Edward Rainger, Worcestershire (GB); Parth Narendran, Birmingham (GB); Helen McGettrick, Birmingham (GB); Myriam Chimen, Birmingham (GB)

(72) Inventors: George Edward Rainger, Worcestershire (GB); Parth Narendran, Birmingham (GB); Helen McGettrick, Birmingham (GB); Myriam Chimen, Birmingham (GB)

(73) Assignee: The University of Birmingham, Birmingham (GB)

( * ) Notice: Subject to any disclaimer, the term of this patent is extended or adjusted under 35 U.S.C. 154(b) by 0 days.

(21) Appl. No.: 14/370,881

(22) PCT Filed: Jan. 14, 2013

(86) PCT No.: PCT/GB2013/050068
§ 371 (c)(1),
(2) Date: Jul. 7, 2014

(87) PCT Pub. No.: WO2013/104928
PCT Pub. Date: Jul. 18, 2013

(65) Prior Publication Data
US 2015/0051137 A1    Feb. 19, 2015

(30) Foreign Application Priority Data
Jan. 13, 2012 (GB) .................... 1200555.9

(51) Int. Cl.
*A61K 38/17* (2006.01)
*A61K 38/10* (2006.01)

(52) U.S. Cl.
CPC .......... *A61K 38/10* (2013.01); *A61K 38/1709* (2013.01)

(58) Field of Classification Search
None
See application file for complete search history.

(56) References Cited

U.S. PATENT DOCUMENTS

2004/0053309 A1    3/2004   Holt et al.
2010/0104587 A1*   4/2010   Chavan et al. ............ 424/174.1

FOREIGN PATENT DOCUMENTS

WO    2008/108842 A1    9/2008
WO    2011/154496 A1   12/2011

OTHER PUBLICATIONS

Yoon et al., "Autoimmune Destruction of Pancreatic β Cells," American Journal of Therapeutics 12:580-591 (2005).*
Weiner, "Multiple Sclerosis Is an Inflammatory T-Cell—Mediated Autoimmune Disease," Arch. Neurol. 61:1613-1615 (2004).*
Ohashi, "T-cell signaling and autoimmunity: molecular mechanisms of disease," Nat. Rev. 2:427-438 (2002).*
Hata, "Distinct contribution of IL-6, TNF-α, IL-1, and IL-10 to T cell—mediated spontaneous autoimmune arthritis in mice," J. Clin. Invest. 114:582-588 (2004).*
Aitken, "14-3-3 proteins: A historic overview," Sem. Canc. Biol. 16:162-172 (2006).*
Chimen et al., "Homeostatic regulation of T cell trafficking by a B cell—derived peptide is impaired in autoimmune and chronic inflammatory disease," Nat. Med. 21:467-475 (May 2015).*
Zandman-Goddard et al., "HIV and autoimmunity," Autoimmun. Rev. 1:329-337 (2002).*
Lim, et al., "Regulation of beta cell survival and function by 14-3-3 proteins," Diabetologia, 2010, vol. 53, Suppl. 1, p. S206.

* cited by examiner

*Primary Examiner* — Julie Ha
*Assistant Examiner* — Kristina M Hellman
(74) *Attorney, Agent, or Firm* — Berliner & Associates

(57) ABSTRACT

Provided is a method for treatment and/or prophylaxis of a condition associated with T cell mediated chronic inflammatory disease by administration, to a patient, of a peptide comprising N'-SVTEQGAELSNEER-C' (SEQ ID NO: 1) or an analog of the peptide that inhibits T cell migration. Also provided is the peptide or its analog for use in the methods of treatment and/or prophylaxis of the condition.

6 Claims, 20 Drawing Sheets

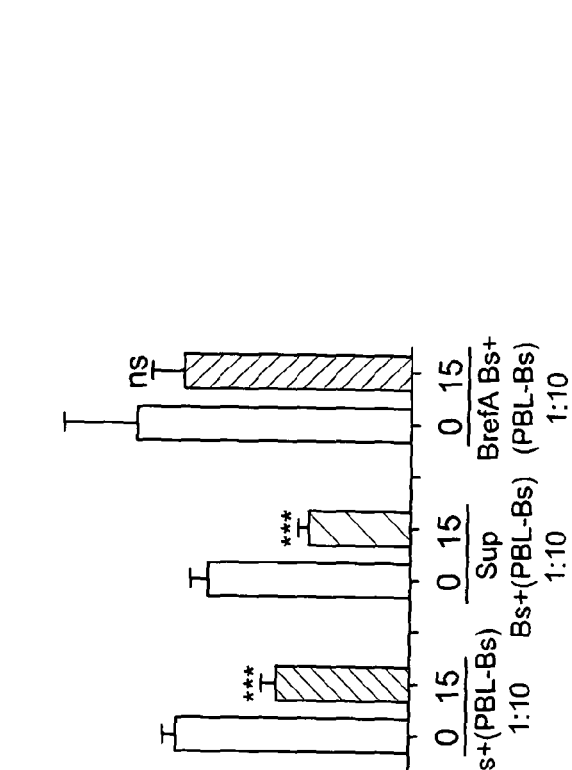
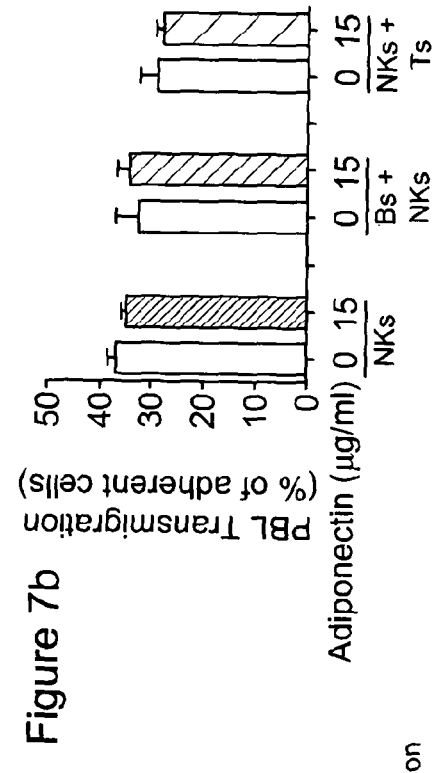
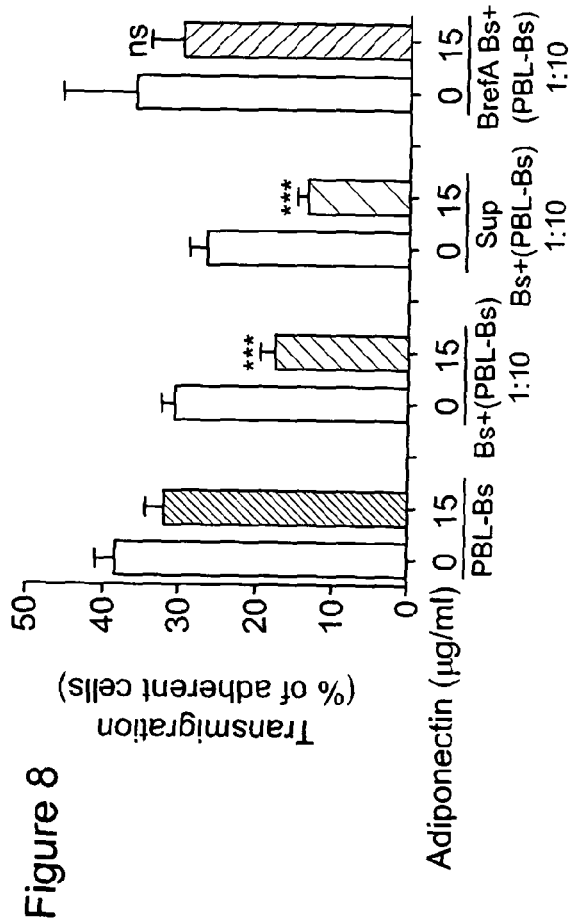
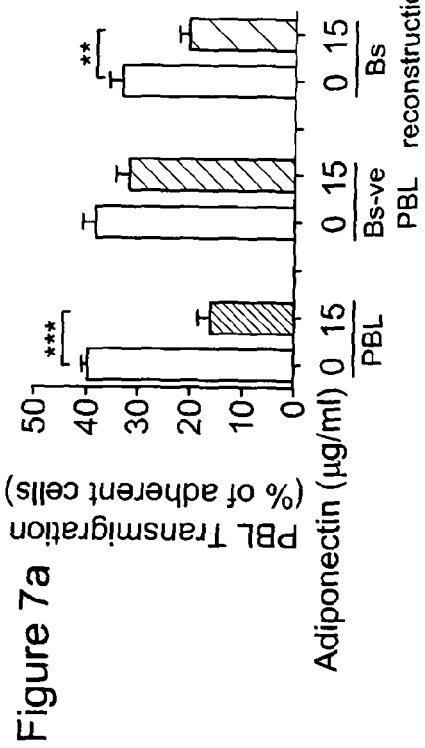

Sequences of 14.3.3. isoforms and presence of the peptide therein.

|  | 10 | 20 | 30 | 40 | 50 | 60 |
|---|---|---|---|---|---|---|
| Beta/Alpha | MTMDKSELVQ | KAKLAEQAER | YDDMAAAMKA | VTEQGHELSN | EERNLLSVAY | KNVVGARRSS |
| Epsilon | MDDREDLVYQ | AKLAEQAERY | DEMVESMKKV | AGMDVELTVE | ERNLLSVAYK | NVIGARRASW |
| Eta | MGDREQLLQR | ARLAEQAERY | DDMASAMKAV | TELNEPLSNE | DRNLLSVAYK | NVIGARRASW |
| Gamma | MVDREQLVQK | ARLAEQAERY | DDMAAAMKNV | TELNEPLSNE | ERNLLSVAYK | NVIGARRASW |
| Sigma | MERASLIQKA | KLAEQAERYE | DMAAFMKGAV | EKGEELSCEE | RNLLSVAYKN | VVGGQRAAWR |
| Theta | MEKTELIQKA | KLAEQAERYD | DMATCMKAVT | EQGAELSNEE | RNLLSVAYKN | VVGGRRSAWR |
| Zeta/Delta | MDKNELVQKA | KLAEQAERYD | DMAACMK SVT | EQGAELSNEE | RNLLSVAYKN | VVGARRSSWR |

|  | 70 | 80 | 90 | 100 | 110 | 120 |
|---|---|---|---|---|---|---|
| Beta/Alpha | WRVISSIEQK | TERNEKKQQM | GKEYREKIEA | ELQDICNDVL | ELLDKYLIPN | ATQPESKVFY |
| Epsilon | RIISSIEQKE | ENKGGEDKLK | MIREYRQMVE | TELKLICCDI | LDVLDKHLIP | AANTGESKVF |
| Eta | RVISSIEQKT | MADGNEKKLE | KVKAYREKIE | KELETVCNDV | L SLLDKFLIK | NCNDFQYESK |
| Gamma | RVISSIEQKT | SADGNEKKIE | MVRAYREKIE | KELEAVCQDV | LSLLDNYLIK | NCSETQYESK |
| Sigma | VLSSIEQKSN | EEGSEEKGPE | VREYREKVET | ELQGVCDTVL | GLLDSHLIKE | AGDAESRVFY |
| Theta | VISSIEQKTD | TSDKKLQLIK | DYREKVESEL | RSICTTVLEL | LDKYLIANAT | NPESKVFYLK |
| Zeta/Delta | VVSSIEQKTE | GAEKKQQMAR | EYREKIETEL | RDIC NDVLSL | LEKFLIPNAS | QAESKVFYLK |

|  | 130 | 140 | 150 | 160 | 170 | 180 |
|---|---|---|---|---|---|---|
| Beta/Alpha | LKMKGDYFRY | LSEVASGDNK | QTTVSNSQQA | YQEAFEISKK | EMQPTHPIRL | GLALNFSVFY |
| Epsilon | YYKMKGDYHR | YLAEFATGND | RKEAAENSLV | AYKAASDIAM | TELPPTHPIR | LGLALNFSVF |
| Eta | VFYLKMKGDY | YRYLAEVASG | EKK NSVVEAS | EAAYKEAFEI | SKEQMQPTHP | IRLGLALNFS |
| Gamma | VFYLKMKGDY | YRYLAEVATG | EKRATVVESS | EKAYSEAHEI | SKEHMQPTHP | IRLGLALNYS |
| Sigma | LKMKGDYYRY | LAEVATGDDK | KRIIDSARSA | YQEAMDISKK | EMPPTNPIRL | GLALNFSVFH |
| Theta | MKGDYFRYLA | EVACGDDRKQ | TIDNSQGAYQ | EAFDISKKEM | QPTHPIRLGL | ALNFSVFYE |
| Zeta/Delta | MKGDYYRYLA | EVAAGD DKKG | IVDQSQQAYQ | EAFEISKKEM | QPTHPIRLGL | ALNFSVFYE |

Figure 9

|            | 190           | 200          | 210        | 220        | 230       | 240         |
|------------|---------------|--------------|------------|------------|-----------|-------------|
| Beta/Alpha | YEILNSPEKA    | CSLAKTAFDE   | AIAELDTLNE | ESYKDSTLIM | QLLRDNLTLW | TSENQGDEGD  |
| Epsilon    | YYEILNSPDR    | ACRLAKAAFD   | DAIAELDTLS | EESYKDSTLI | MQLLRDNLTL | WTSDMQGDGE  |
| Eta        | VFYYEIQNAP    | EQACLLAKQA   | FDDAIAELDT | LNEDSYKDST | LIMQLLRDNL | TLWTSDQQDE  |
| Gamma      | VFYYEIQNAP    | EQACHLAKTA   | FDDAIAELDT | LNEDSYKDST | LIMQLLRDNL | TLWTSDQQDD  |
| Sigma      | YEIANSPEEA    | ISLAKTTFDE   | AMADLHTLSE | DSYKDSTLIM | QLLRDNLTLW | TADNAGEEGG  |
| Theta      | ILNNPELACT    | LAKTAFDEAI   | AELDTLNEDS | YKDSTLIMQL | LRDNLTLWTS | DSAGEECD AA |
| Zeta/Delta | ILNSPEKACS    | LAKTAFDEAI   | AELDTLSEES | YKDSTLIMQL | LRDNLTLWTS | DTQGDEAEAG  |

| | |
|---|---|
| Beta/Alpha | AGEGEN (SEQ ID NO: 4) |
| Epsilon | EQNKEALQDV EDENQ (SEQ ID NO: 5) |
| Eta | EAGEGN (SEQ ID NO: 6) |
| Gamma | DGGEGNN (SEQ ID NO: 7) |
| Sigma | EAPQEPQS (SEQ ID NO: 8) |
| Theta | EGAEN (SEQ ID NO: 9) |
| Zeta/Delta | EGGEN (SEQ ID NO: 10) |

Figure 9 (Continued)

PEPTIDE AND USES THEREFOR

REFERENCE TO SEQUENCE LISTING

A Sequence Listing is submitted electronically via EFS-Web as an ASCII formatted text file with the name "7492123ST25"; the file was created Nov. 13, 2015, is 16 kilobytes in size and is incorporated herein by reference in its entirety.

BACKGROUND

The present invention relates to use of a peptide secreted from B cells that has an inhibitory effect on the migration of T cells (including auto-reactive T cells). This has applications in the treatment and/or prophylaxis of the conditions associated with such T cells, most notably type 1 diabetes mellitus.

INTRODUCTION

Pancreatic islet-reactive T cells play a central role in beta cell destruction and thus in the pathogenesis of type 1 diabetes (T1D). In evidence, T cells comprise a major part of the islet infiltrate in a T1D pancreas, and immunosuppressive drugs that target T cells preserve beta cell function. Understanding the mechanisms by which islet-reactive T cells are recruited from the blood, across inflamed endothelium, and into the pancreatic islet have been poorly examined in T1D.

This is particularly relevant because healthy humans can also have circulating islet reactive T cells that do no apparent harm. Therefore, we believe that in T1D, endogenous mechanisms that prohibit the trafficking of reactive T cells into the pancreas fail, and if such regulatory pathways could be re-established it may be possible to exclude auto-reactive T cells and preserve beta cell function. The adipocyte-derived cytokine, adiponectin, has a role to play in regulating T cell migration, but the picture is more complex than that as adiponectin's circulating levels do not seem to fluctuate in T1D.

Surprisingly, we have found that a certain peptide can inhibit T cell migration. Although this peptide is known, what we have shown is that adiponectin achieves its effects on T cell migration by the induction of a mediator released from B lymphocytes. This mediator, a peptide, appears to be an inhibitor of T cell trans-endothelial migration.

SUMMARY OF THE INVENTION

The peptide has the sequence N'-SVTEQGAELSNEER-C' (SEQ ID NO: 1) or is an analogue thereof that inhibits T lymphocyte migration.

Thus, in a first aspect, the present invention provides a method for treatment and/or prophylaxis of a condition associated with T cell mediated chronic inflammatory disease by administration of a peptide comprising N'-SVTEQGAELSNEER-C' (SEQ ID NO: 1) to a patient in need thereof. The peptide may also be an analogue or variant thereof that inhibits T lymphocyte migration.

The condition is, optionally, selected from the group consisting of T cell auto-reactivity, T cell mediated chronic inflammatory disease and autoimmune disease. Alternatively, the condition may be T cell auto-reactivity or T cell mediated chronic inflammatory disease or autoimmune disease.

It will be appreciated that the terms T cell and T lymphocyte can be interchanged herein. The migration of the T cells is, optionally, trans-endothelial. The endothelium is, optionally, that of the pancreatic microvasculature that separates the islet cells from the blood supply.

The peptide is, optionally, an isolated peptide. The peptide may be synthesized (i.e. chemically synthesized, for instance in the same way as a small molecule pharmaceutical) or it may be produced recombinantly, for instance in a separate cellular system (cell culture) or animal.

The amino acid sequence of the peptide that we have found to be useful is SVTEQGAELSNEER (SEQ ID NO: 1). This sequence may be comprised within a larger peptide or protein, or a chimaeric or fusion protein. Alternatively, the peptide may consist solely of SEQ ID NO: 1. All of these fall within the definition of the peptide as used herein. The peptide according to SEQ ID NO: 1 represents amino acids 28-41 of the 14.3.3 zeta/delta (14.3.3.ζδ) protein, which in turn is a 245 amino acid product of the YWHAZ gene.

It is also preferred that analogues or variants of the peptide can be used. Particularly preferred in this respect are analogues (or variants) based on conservative amino acid substitutions. The preferred peptide is 14 amino acids long, although the peptide can also be as few as 13, 12, 11 or 10 amino acids or as many as 15, 16, 17 18, 19 or 20 amino acids. Where amino acids are added or removed, these are preferably to or from the N and/or C terminus of the peptide. Other modifications to the chemical structure that protect the peptide from degradation or clearance in vivo are also preferred variants, for example but not restricted to, PEGylation which utilises a linker or spacer as is known in the art. Most preferably, any analogue should retain or improve upon the desired function, namely the inhibition of T cell migration, compared to SVTEQGAELSNEER (SEQ ID NO: 1). This may be through changes in affinity for cognate receptor(s) or changes that alter the pharmacokinetic profile of the peptide in vivo. It will be appreciated that it is now within the skill of the art to modify peptide chemistry to increase the pharmacological 'profile' of peptides in vivo, and that these changes are not based solely on amino acid substitution.

Reference herein will be made to the peptide, but it will be understood that this also encompasses any analogues thereof, unless otherwise apparent.

The action of the peptide may be as an agonist of its cognate receptor(s).

The inhibition of the migration of the T cells may be the recruitment of said cells to the pancreas, for instance from the blood.

Optionally, the T cells are auto-reactive T cells. These may preferably target the pancreas, especially the islet cells of the pancreas. The T cells may be CD4+ or CD8+.

In a particularly preferred embodiment, the peptide serves to inhibit (i.e. reduce) the recruitment of auto-reactive T cells to the islets of the pancreas.

It will be appreciated that the peptide acts upon the individual to which it is administered. As such, the auto-reactivity of any T cells is reactivity against self (i.e. islet cells of the pancreas) from that individual. The individual is a mammal, optionally, a rodent such as a rat or mouse, or a primate, particularly an ape or human.

As the presence of the peptide serves to inhibit the migration of the T cells, increasing the amount of peptide that the individual is exposed to will serve to further inhibit said migration. Optionally, the level of inhibition of migration is such that migration is reduced by at least 50% (in terms of numbers of T cells that are recruited), but most preferably this reduction is at least 60%, more preferably at least 70%, more preferably at least 80%, more preferably at least 90%, more preferably at least 95%, more preferably at least 99% and most preferably reduced to negligible levels. Ideally, of course, no T cells will migrate but this may not be realistic and in fact, all that is required is that normal function of the target tissue, for instance the islet cells, is largely preserved and/or returned (or at east as close to normal levels as possible or desirable to alleviate the condition to be treated).

The present peptide is most useful, therefore, in treating a number of conditions. These include those in which T cells play a role in pathology or conditions associated with T cell auto-reactivity. These may include T cell mediated chronic inflammatory disease and autoimmune disease. Diabetes mellitus (type 1), is particularly preferred. Also envisaged are juvenile onset diabetes, rheumatoid arthritis and Crohn's disease, atherosclerosis, psoriasis, inflammatory and fibrotic liver disease(s) including steatohepatitis and cirrhosis and uveitis. The peptide therefore preferably functions to treat any of the above, but most preferably type 1 diabetes (T1D). The peptide may be considered as serving to rescue or preserve residual pancreatic function. This may be lost function that has occurred due to attack by the auto-reactive T cells. The peptide may be considered as serving to improve diabetic outcomes, i.e. a reduction in the symptoms of T1D. The peptide may also be considered as serving to improve other morbidities associated with loss of pancreatic function which include renal (e.g. nephropathy; diabetic kidney disease), neurological (e.g. peripheral neuropathy) and cardiovascular complications (e.g. diabetic retinopathy and cardio-cerebral disease due to accelerated atherosclerosis), associated with the loss of pancreatic function (in turn) associated with T1D. Therefore, the peptide may be most useful in the treatment and/or prophylaxis of the above conditions, particularly T1D and its co-morbidities (as described).

The invention also provides a polynucleotide sequence coding for said peptide, which is also useful in the treatment and/or prophylaxis of any of the above conditions. The polynucleotide may be DNA, RNA or a DNA/RNA hybrid. This polynucleotide encodes the peptide or its analogue. Although there are a considerable number of possible combinations, we provide at least two examples of a polynucleotide that encode the amino acid sequence of SVTEQ-GAELSNEER (SEQ ID NO: 1). These are:

```
                                            (SEQ ID NO: 2)
5'-AGU GUU ACU GAA CAA GGU GCU GAG UUA UCU AAU GAG

GAG AGA-3';
or
                                            (SEQ ID NO. 3)
5'-AGC GUC ACC GAG CAG GGC GCC GAA UUG UCC AAC GAA

GAG AGG-3',
```

The above sequences are only examples, and are given in RNA form, but the invention also provides for the DNA form (with T replacing U) and DNA/RNA hybrid form thereof, as well as the complementary sequences of both the RNA, DNA and RNA/DNA hybrid forms (the complementary sequences being in RNA, DNA or DNA/RNA). Variants having at least 80% sequence homology are preferred, the variant encoding a peptide that is at least 50%, for instance, as efficacious as SEQ ID NO: 1. Variants have at least functions 85% sequence homology, at least 90% sequence homology, at least 95% sequence homology, at least 99% sequence homology are also preferred (rounding to the nearest whole number). This may be determined by programs such as BLAST, for instance.

Also provided is a plasmid (i.e. a construct), comprising the polynucleotide which encodes the peptide (or its analogue or variant). The polynucleotide is preferably operably linked to a suitable promoter. The promoter may be a pancreas-specific promoter, for instance.

The polynucleotide encoding the peptide may be delivered by administration of a suitable vehicle containing the polynucleotide or to which it is bound. Examples include a so-called gene gun where the polynucleotide may be attached to a gold particle fired through the skin. Alternatively, and more preferably, the polynucleotide (for instance a plasmid comprising it) could be encapsulated within a viral vector or capsid. Preferred examples include adenoviral vectors. Those that target the pancreas are preferred.

Administration of the peptide may be by delivery of the peptide per se, for instance in the form of a pharmaceutically acceptable formulation, or by delivery and expression of the polynucleotide encoding the peptide, for instance in the forms described above. These may be delivered, for instance to the blood, by injection. This may be intramuscularly or subcutaneously. These may also be delivered via a mucosa, such as the oral, nasal or rectal mucosa. These may also be delivered in the form of a spray or tablet or in the form of a suppository. These may also be ingested orally into the stomach although in the case of the peptide this may require the provision of the peptide in a pro-drug form to alleviate or combat the effects of the GI digestion.

Although useful in one aspect, it will be appreciated that that it is not necessarily the case that that the peptide or the polynucleotide encoding it is, or needs to be, targeted at or to the pancreas (at least for T1D). Optionally, therefore, for peptide delivery, increasing systemic presentation in the blood plasma is all that is required. Delivery specifically to the pancreas is not required. Nevertheless, in an alternative embodiment, delivery specifically to the pancreas may be used as this could increase efficacy. The same applies for the polynucleotide.

Direct targeting to the pancreas is envisaged, as part of a targeted gene therapy including the polynucleotide encoding the peptide.

Also provided is a pharmaceutically-acceptable composition or preparation comprising the peptide, the polynucleotide, the plasmid or the viral vector described herein. Optionally, the pharmaceutically-acceptable composition comprises the peptide and is suitable for injection or ingestion.

As explained above, methods of treatment and/or prophylaxis of the conditions above are envisaged, particularly conditions associated with T cell mediated chronic inflammatory disease, including T cell auto-reactivity, T cell mediated chronic inflammatory disease and autoimmune disease. Diabetes mellitus (type 1), is particularly preferred. Also envisaged are juvenile onset diabetes, rheumatoid arthritis and Crohn's disease, atherosclerosis, psoriasis, inflammatory and fibrotic liver disease(s) including steatohepatitis and cirrhosis and uveitis, as well as any of the above-mentioned morbidities. The methods may comprise administering to a patient in need thereof a therapeutic amount of the peptide or polynucleotide in any of the manners described herein.

Thus, provided is a method of treatment and/or prophylaxis of a condition associated with T cell mediated chronic inflammatory disease, including T cell auto-reactivity, T cell mediated chronic inflammatory disease and autoimmune disease. In particular, the condition is diabetes mellitus (type 1). However, the condition may also be selected from the group consisting of: juvenile onset diabetes; rheumatoid arthritis; Crohn's disease; atherosclerosis; psoriasis; inflammatory and fibrotic liver disease(s) including steatohepatitis and cirrhosis; and uveitis; or the condition may be selected from the group consisting of nephropathy; diabetic kidney disease; peripheral neuropathy; diabetic retinopathy; and cardio-cerebral disease.

The methods may be for the treatment of said conditions or of the treatment of said conditions. Alternatively, the methods may be for the prophylaxis of said conditions or may be of prophylaxis of said conditions. Alternatively, the methods may be any combination thereof.

Also provided is the peptide and/or the polynucleotide encoding it for use in the treatment and/or prophylaxis of the conditions descried herein. Reference herein to methods includes such use.

BRIEF DESCRIPTION OF THE FIGURES

The invention will now be described with reference to the Figures where:

FIG. 1a is a graph of PBL transmigration versus adiponectin amount, FIG. 1b is a graph of PBL transmigration versus log of adiponectin (AQ) concentration, and FIG. 1c is another graph of PBL transmigration versus adiponectin concentration;

FIG. 3: PBL from T1D patients are released from the inhibitory effect of adiponectin on transendothelial cell migration.

FIG. 4: The expression of adiponectin receptors on PBL is reduced in patients with T1D.

FIG. 5: The expression of adiponectin receptors in T1D or healthy control subjects correlates with the inhibition of lymphocyte migration by Adiponectin.

FIG. 6: The expression of adiponectin receptors on different leukocyte subsets.

FIG. 7: B cells mediate the adiponectin-induced inhibition of T cell migration; FIG. 7a is a graph of transmigration for various cell samples; FIG. 7b is another graph of transmigration for various cell samples;

FIG. 8: B cells modulate PBL transmigration through secretion of a peptide;

FIG. 9 shows the sequence of the secreted peptide and different isoforms of the 14.3.3 proteins;

FIG. 11: The peptide inhibits T cell migration across endothelial cells in vitro.

15 μg/ml of Aq significantly reduced lymphocyte migration across endothelial cells. removing B cells from the peripheral blood lymphocyte preparation completely inhibited this response. This could be reconstituted using supernatants from Aq stimulated B cells could also effectively inhibit lymphocyte migration, but this effect was lost when supernatants were prepared in the presence of Brefeldin-A, an inhibitor of B cell secretion. These data demonstrate that a soluble mediator released from B cells is required.

Figure 15:
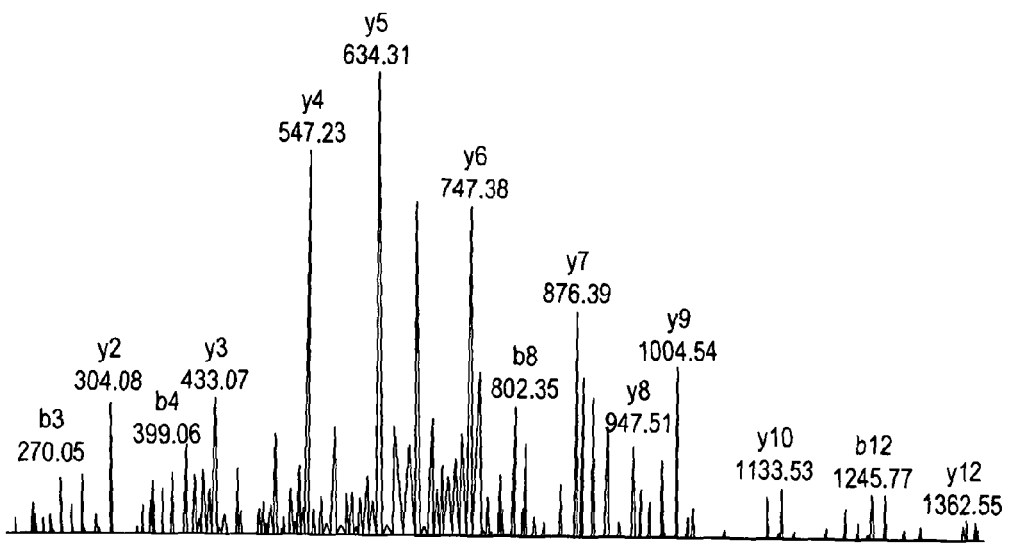
Figure 16:
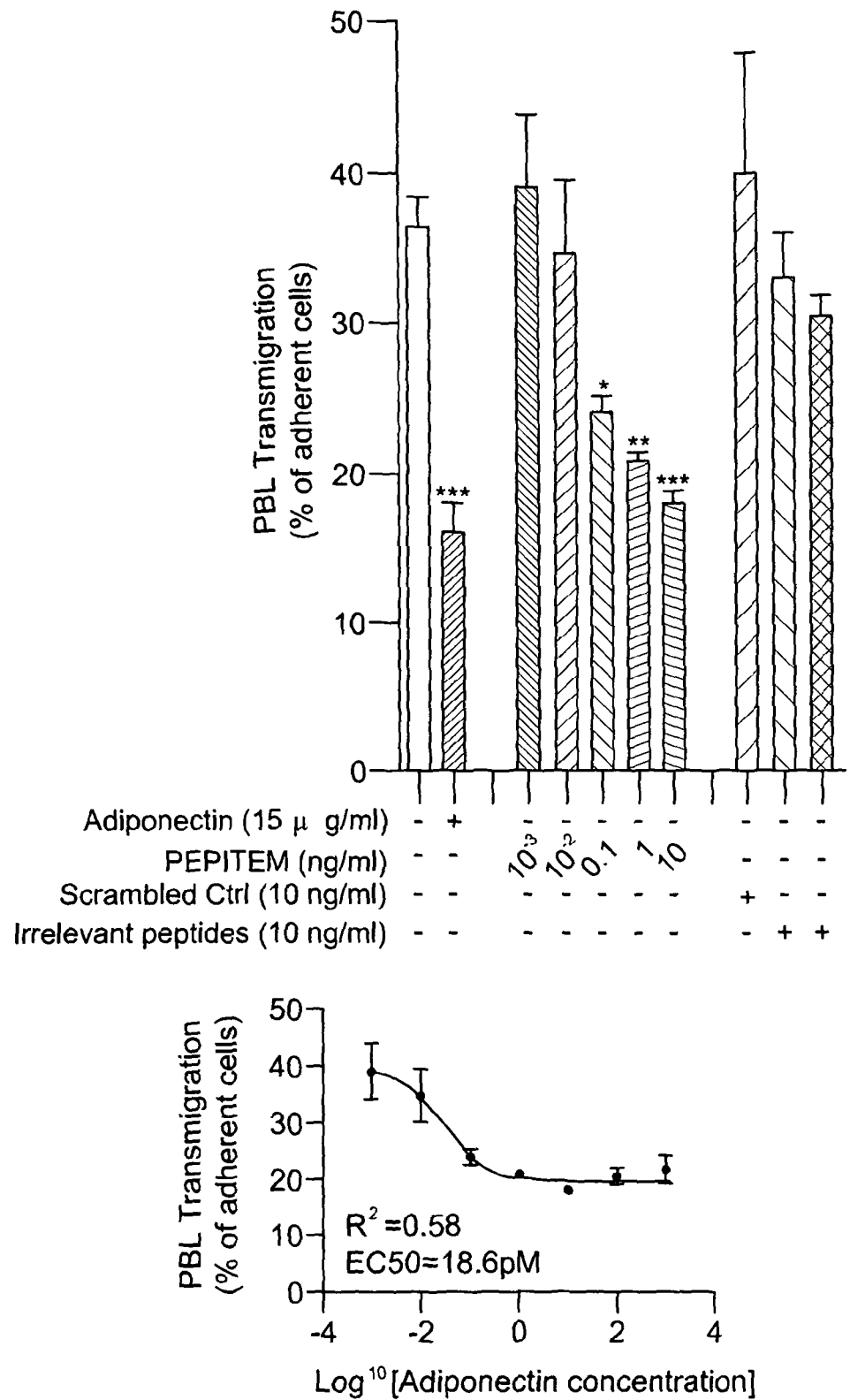

FIG. 15: a 14 amino acid peptide released from B cells regulates T cell trafficking FIG. 16: PEPITEM inhibits T cells transmigration
  A) The synthetic peptide was highly effective at inhibiting the transmigration of lymphocytes, while control peptides, including a scrambled version (randomized reorganisation of the native peptide sequence), were ineffective at inhibiting lymphocyte migration.
  B) The peptide had an EC50 of ≈20 pM. As it effectively inhibited lymphocyte migration across endothelial cells, we called the agent PEPtide Inhibitor of Trans Endothelial Migration; "PEPITEM."

Figure 17A:
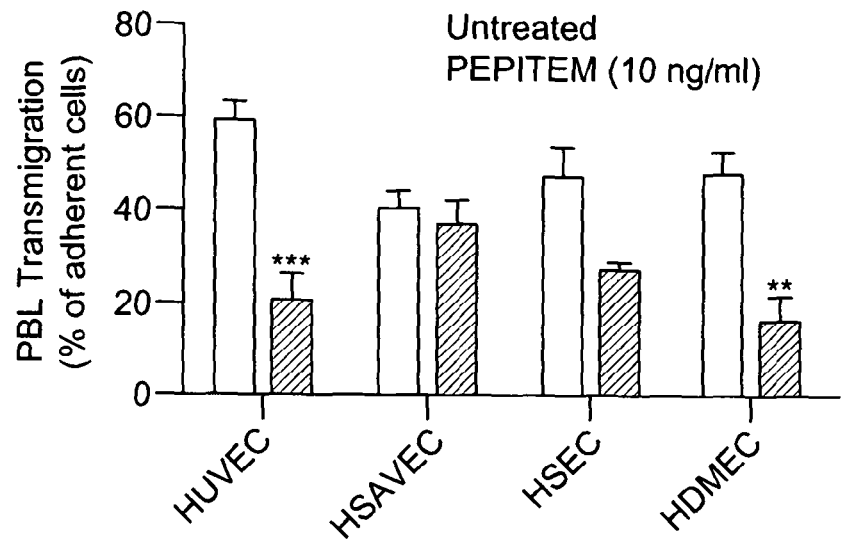
Figure 17B:
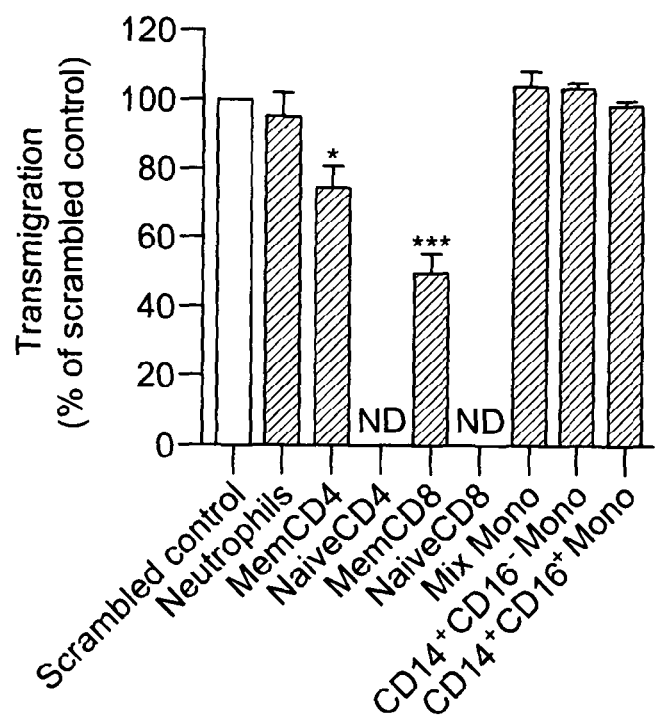
Figure 17C:
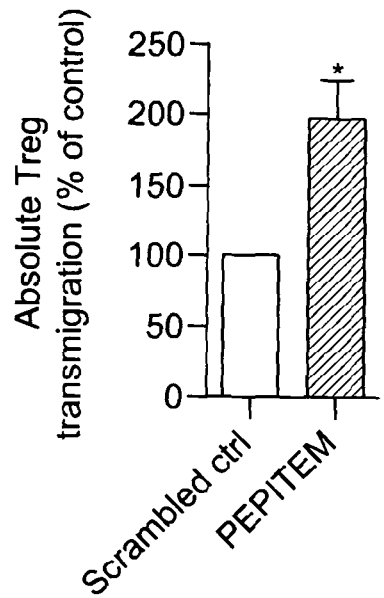

FIG. 17: PEPITEM inhibits T cell migration AND promotes the recruitment of anti-inflammatory regulatory T cells PEPITEM inhibits T cell migration across EC with the same pattern as adiponectin (A); It is effective at inhibiting the migration of memory CD4+ and CD8+ T cells, but it has no effect neutrophils, or monocytes (including CD16− and CD16+ subsets. Naïve lymphocytes were not assessed in this analysis as they do not adhere to the endothelial cell monolayer (B). Interestingly, the efficiency of the migration of regulatory T cells (T-regs), which have anti-inflammatory functions, was increased by PEPITEM (C).

Figure 18:
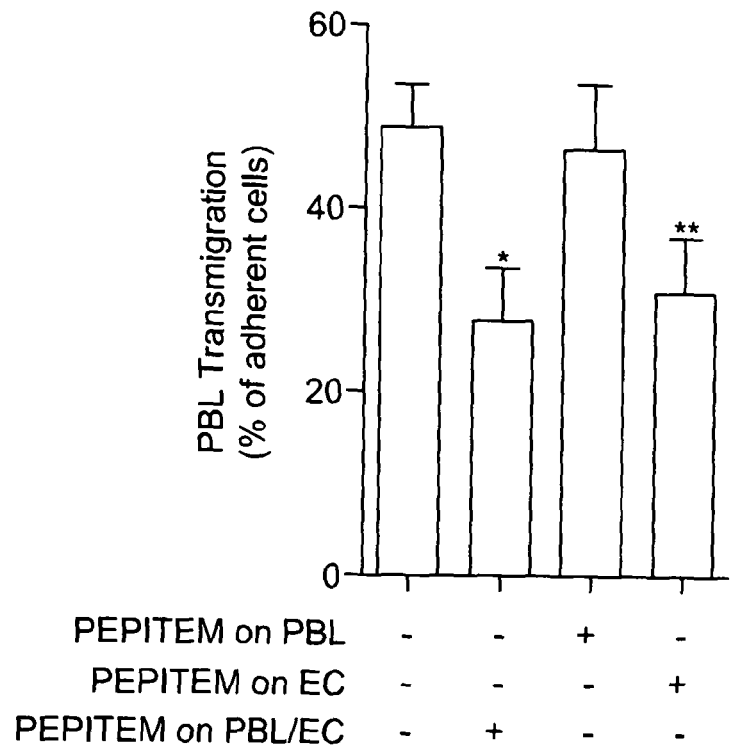
Figure 19A:
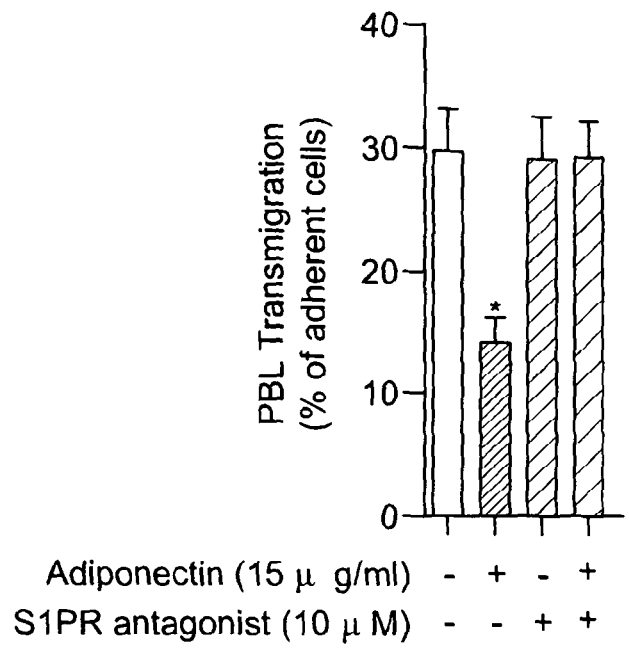
Figure 19B:
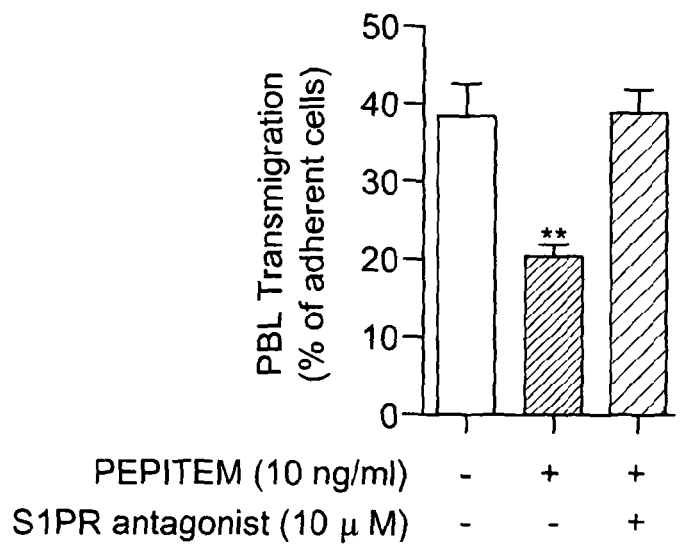
Figure 19C:
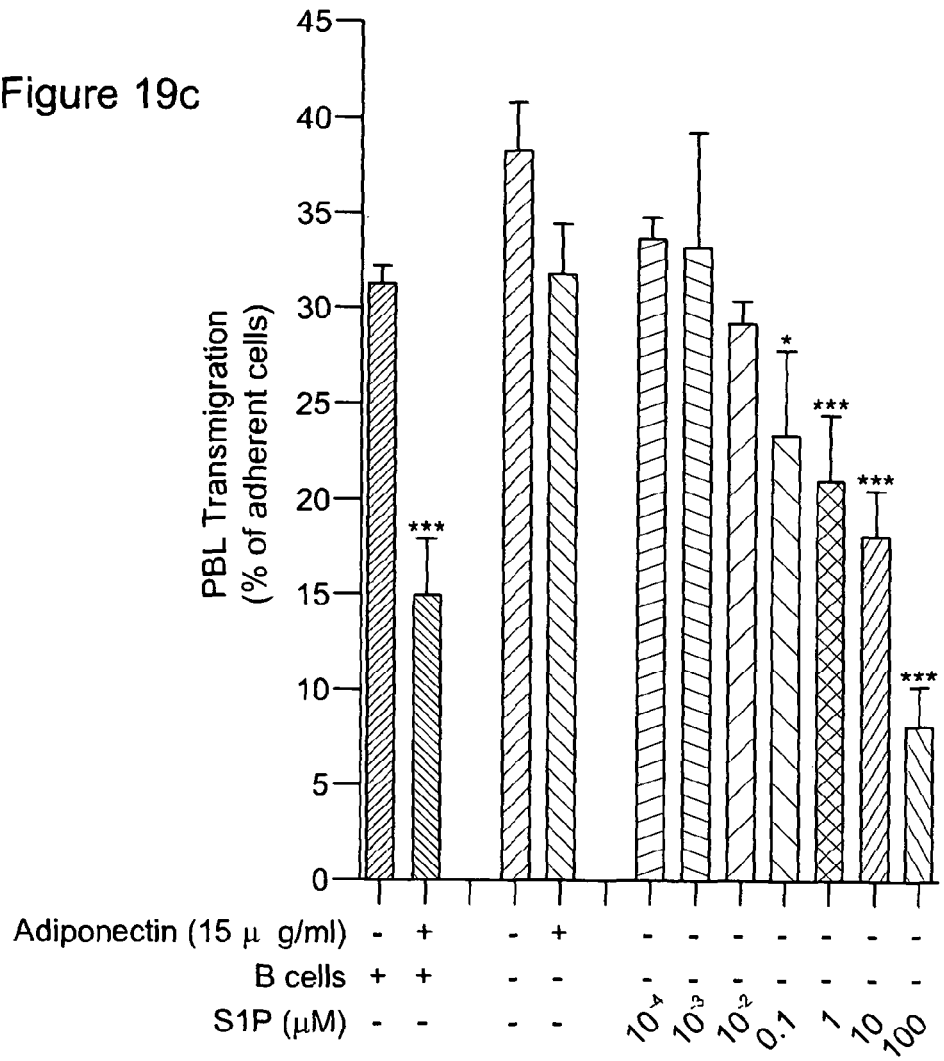
Figure 19D:
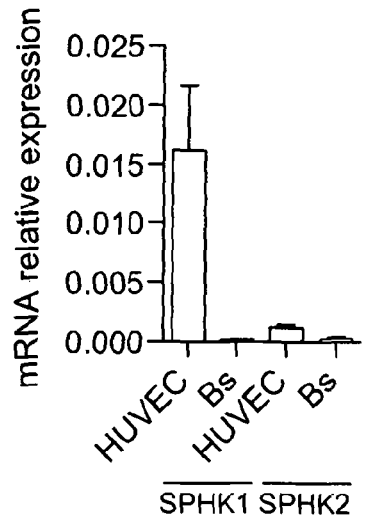
Figure 19E:
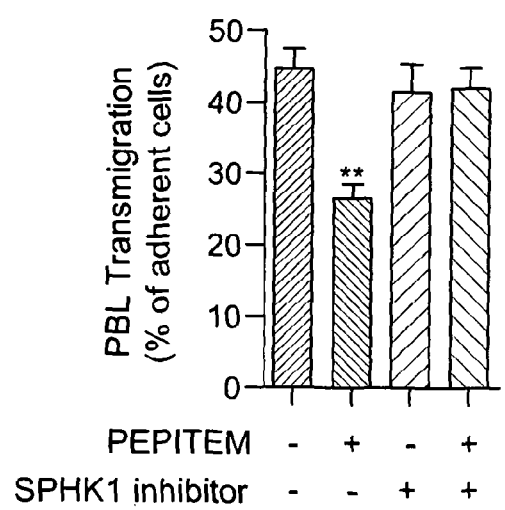

FIG. 18: PEPITEM does not directly regulate T cell migration.

Again the most obvious mode of action of PEPITEM was by directly regulating the migratory functions of T cells. However, this was not the case. When PBL were treated with PEPITEM and the agent was washed away prior to assay on endothelium, the efficiency of lymphocyte migration was not effected. However, pre-treating the endothelial cells with PEPITEM resulted in inhibition of lymphocyte trafficking. Thus, PEPITEM operates by stimulating endothelial cells to release an agent that inhibits T cell trafficking.

FIG. 19: The induction of sphingosine-1-phosphate (SIP) synthesis by endothelial cells inhibits T cell migration.

As PEPITEM did not directly inhibit lymphocyte migration we tested the hypothesis that a known regulator of lymphocyte trafficking in other tissues, sphingosine-1-phosphate (S1P), was the terminal step in this pathway.

Figure 20A:
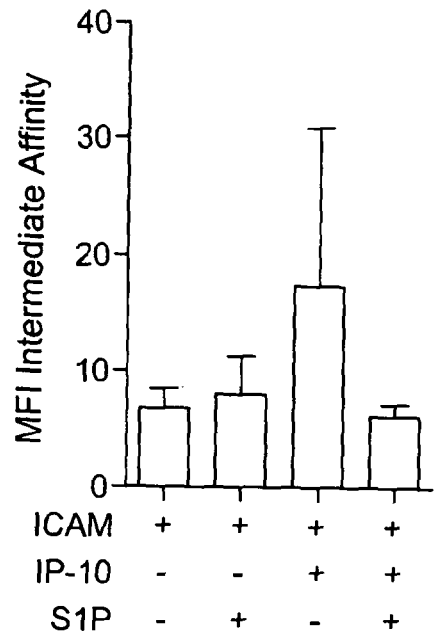
Figure 20B:
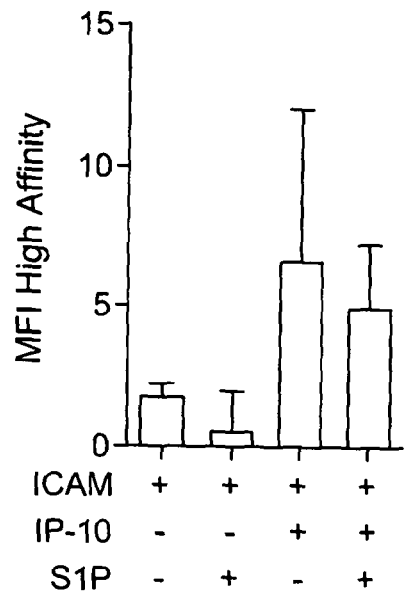

A) A S1P-receptor antagonist (W146), releases lymphocytes from the inhibitory effects of adiponectin
B) A S1P-receptor antagonist (W146), releases lymphocytes from the inhibitory effects of PEPITEM
C) Addition of exogenous S1P dose dependently inhibits T cell migration
D) Endothelial cell express sphingosine kinase-1 (SPHK1) but not sphingosine kinase-2 (SPHK2)
E) An inhibitor of SPHK1 releases lymphocytes from the inhibitory effects of PEPITEM FIG. 20: S1P regulates the affinity of the lymphocyte integrin LFA-1 (CD11a/CD18; αLβ2) when the cells are immobilised on ICAM and activated with IP10 (CXCL10)
(A) KIM127 for the intermediate affinity site and
(B) antibody 24 for the high affinity epitope on memory T cells treated with S1P.

Figure 21A:
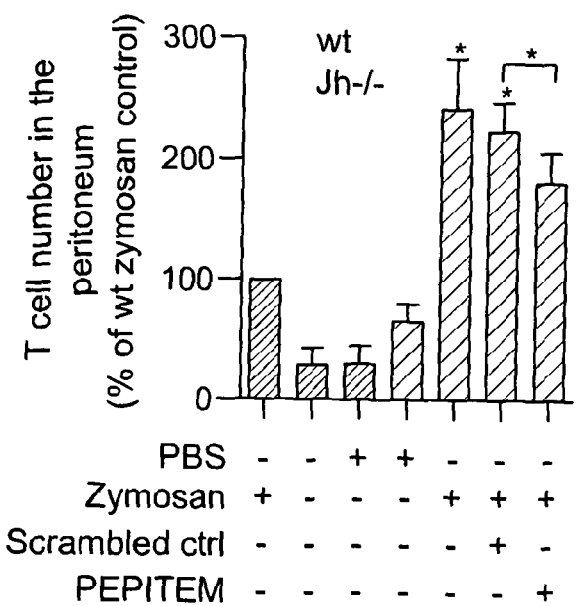
Figure 21B:
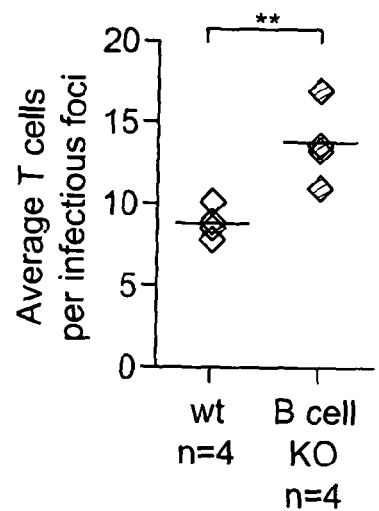
Figure 22A:
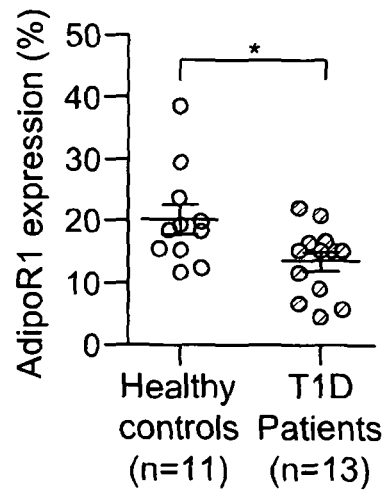
Figure 22B:
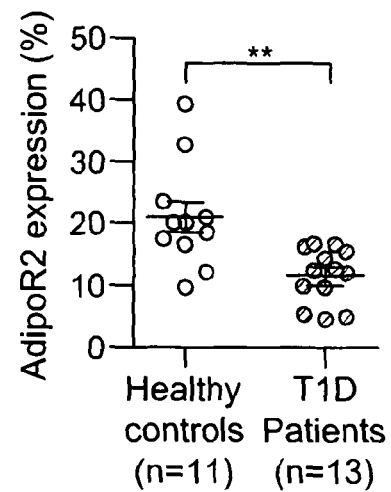
Figure 22C:
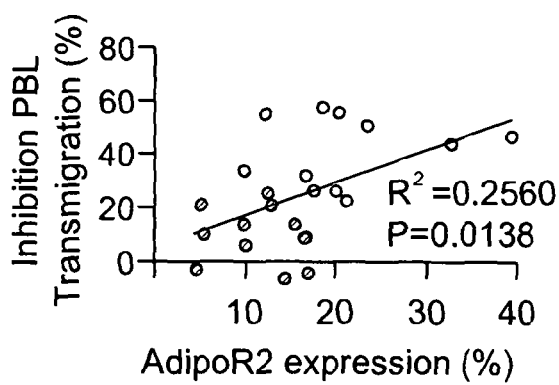
Figure 22D:
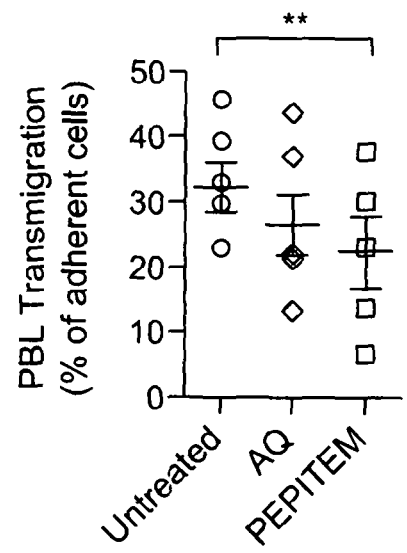

FIG. 21: Absolute number of T cells in the inflamed peritoneum of wild type or B cell knockout mice in the presence or absence of the peptide.

A The recruitment of T cells into the peritoneum of Jh−/− (B-cell knockout animals) was greater at baseline (i.e. after challenge with PBS) than wild type animals. After challenge with intraperitoneal injection with zymosan T cells Numbers increased in the wild type animals. There was a dramatic and significant increase I T cell number in the B cell knockout mice and this was significantly reduced in the presence of PEPITEM, but not the scrambled peptide.

B The recruitment of T cells into the liver of B-cell knockout animals after challenge with none-typhoidal *salmonella* infection increased when compared to the wild type animals.

FIG. 22: The adiponectin/PEPITEM pathway is altered in patients with type 1 diabetes In type-1-diabetic patients the expression of adiponectin receptors is significantly reduced compared to healthy aged matched controls (A and B). The inhibition of lymphocyte trafficking by adiponectin correlates significantly with the level of expression of adiponectin receptors on B cells (C), so that patient and healthy cohorts separate Into discrete clusters on the correlation graph. Importantly, although patient lymphocyte are refractory to stimulation by adiponectin (D), the inhibitory pathway can be recapitulated for these cells by addition of exogenous PEPITEM

DETAILED DESCRIPTION OF THE INVENTION

WO2007127935 relates to the histone deacetylase, HDAC7. It sets out to identify the phosphatase that dephosphorylates HDAC7 and finds that a number of proteins bound to HDAC7, including the peptide described herein as SEQ ID NO: 1. The focus of the document is that a "target subunit" of the myosin phosphatase (MYPT1) also bound HDAC7 and as such the teaching is directed to the interaction between HDAC7 and Myosin Phosphatase via this subunit of myosin phosphatase. There is no mention that our peptide has any value, nor that it interferes with the HDAC7-Myosin Phosphatase interaction. US2002164668 (A1) and US20030064411 (A1) disclose our peptide and pharmaceutical preparations/compositions comprising it in relation to the treatment of Alzheimer's disease. US20040053309 (A1) also discloses our peptide, but relates to the identification of proteins and protein isoforms that are associated with kidney response to toxic effectors. However, none of the prior art discloses the use of our peptide or analogues thereof.

Figure 1:
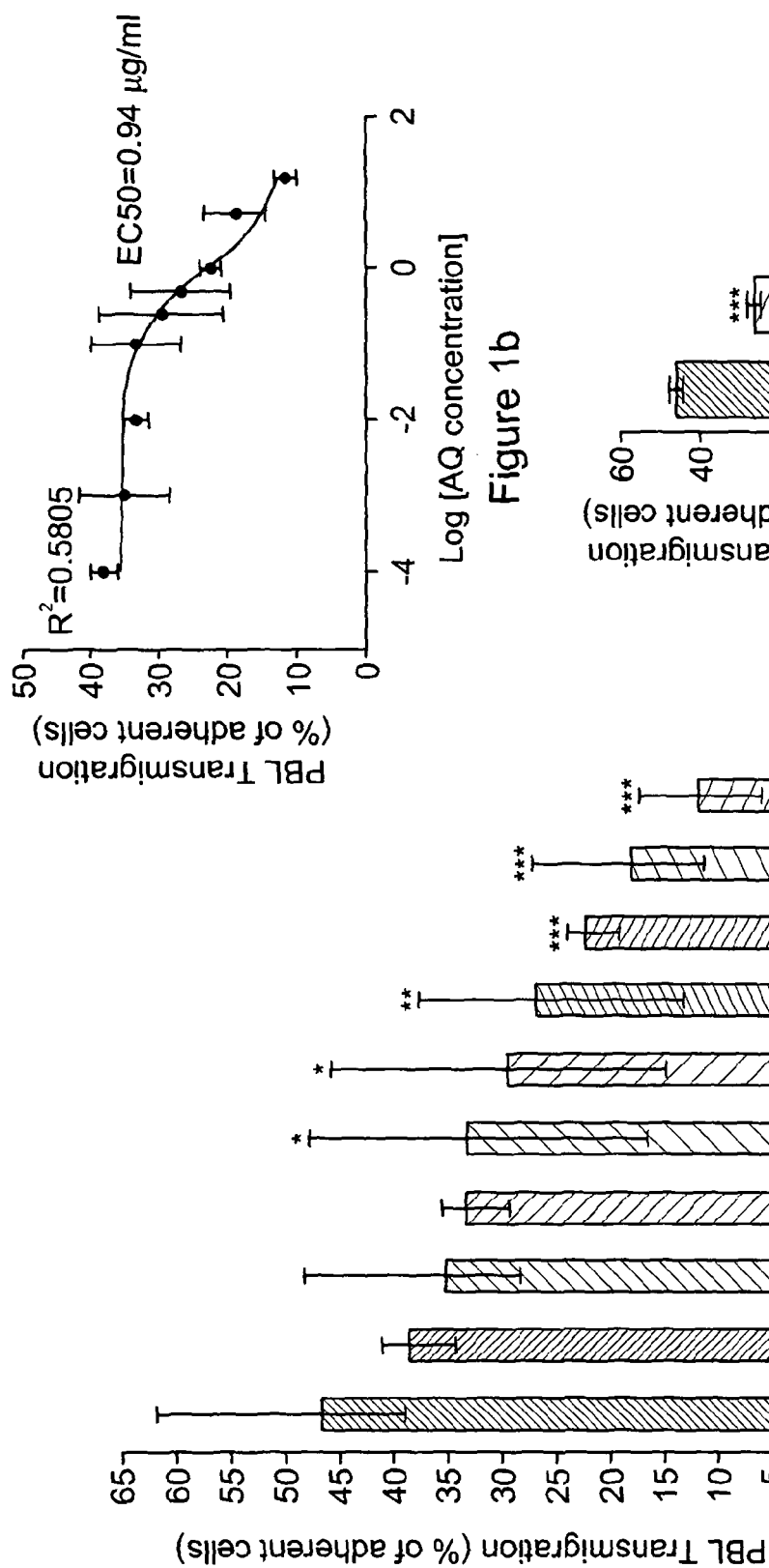
FIG. 1: Adiponectin inhibits the transendothelial cell migration of peripheral blood lymphocytes (PBL)

We have been interested in the ability of the adipocyte derived cytokine, adiponectin, to regulate the recruitment of human T cells to inflamed endothelium. Previously, adiponectin deficient mice were shown to have a two-fold increase in leukocyte adhesion to endothelial cells and importantly, leukocyte recruitment was normalized by the addition of recombinant adiponectin. In our in vitro studies we used static transwell assays, as well as flow based adhesion assays, to track the migration of T cells (which were in crude isolates of peripheral blood lymphocytes [PBL]) across TNF-α and IFN-γ stimulated endothelial cells. T cell migration was dose dependently blocked by adiponectin (FIG. 1).

Figure 2:
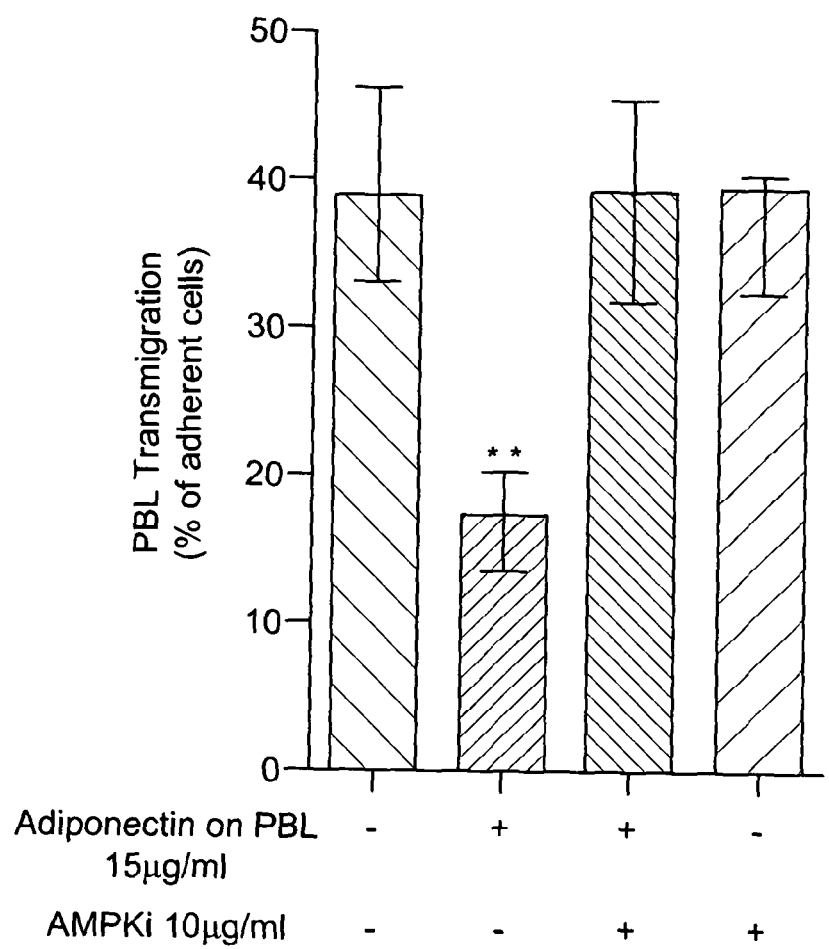
FIG. 2: Inhibition of AMPK with compound C restores the migration of PBL.

The effect of adiponectin on T cell transmigration was mediated by signalling through the adiponectin receptors (AR1 and AR2). AMP-activated protein kinase (AMPK) is a crucial intermediate in the down stream signalling from AR1 and AR2 and when PBL were pre-treated for 30 minutes with the AMPK inhibitor, compound C, the effects of adiponectin on the inhibition of T cell migration were ablated, i.e. T cell migration returned to the levels observed in the absence of adiponectin (FIG. 2). Compound C did not have any effects on migration in the absence of adiponectin.

Figure 3A:
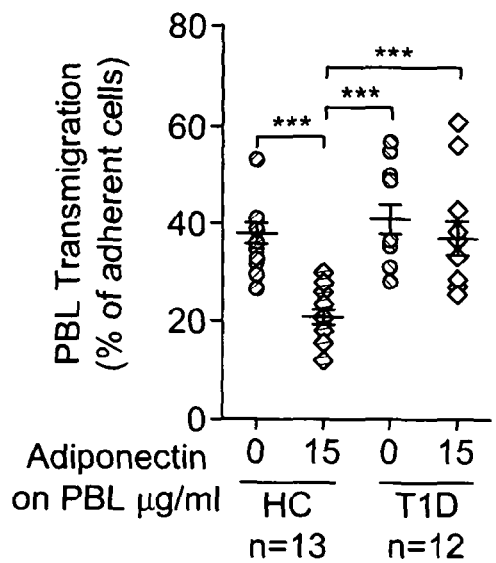
FIG. 3a is a graph of PBL transmigration in T1D and control samples.
Figure 3B:
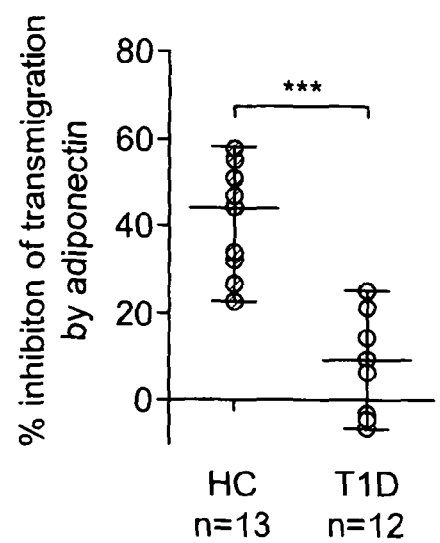
FIG. 3b is a graph of % inhibition of PBL transmigration in T1D and control samples.

Importantly, we found that the adiponectin mediated inhibition of T cell migration was significantly compromised in patients with T1D i.e., the ability of adiponectin to modulate T cell recruitment in our in vitro migration assays was lost when PBL isolated from T1D were used (FIG. 3). We have now shown that both AR1 and AR2 are significantly down regulated on lymphocytes in T1D (FIG. 4), and the levels of adiponectin mediated inhibition of T cell migration in vitro correlate exquisitely with expression of these receptors in T1D, to the extent that patient and healthy control cohorts cluster independently when receptor density is plotted against sensitivity to adiponectin in the endothelial cell transmigration assay (FIG. 5).

We do not believe that adiponectin represents a suitable target for regulating T cell recruitment in T1D. Its concentration in the circulation is not altered in T1D, indicating that aspects of adiponectin biology other than its bioavailability are important arbiters of function. Moreover, adiponectin is a pleiotropic agent with important roles in metabolic homeostasis, raising the possibility of serious off target side effects.

Rather, we believe that targeting pathways down stream of adiponectin, which regulate T cell migration, would provide a therapeutic modality of greater precision. Thus, we have now gone on to show unequivocally that adiponectin achieves its effects on T cell migration by the induction of a novel mediator, which we believe is a peptide inhibitor of trans-endothelial migration that is released from B lymphocytes. Importantly, B lymphocytes express adiponectin receptors, so can respond in an appropriate manner to stimulation by this agent (FIG. 6).

Moreover, the inhibition of T cell migration by adiponectin is lost if B cells are removed from mixed lymphocyte preparations (PBL), and inhibition of T cell migration is regained if isolated B cells are added to purified preparations of T cells (FIG. 7a). Interestingly, natural killer lymphocytes (NK cells), which also express high levels of adiponectin receptors (FIG. 6) are not capable of regulating the migration of T cells (FIG. 7b), indicating that the regulation of T cell migration is mediated exclusively by B lymphocytes and not other cellular components of the PBL population.

B cells mediate their effects in this system by secretion of the peptide. Thus, supernatants conditioned by adiponectin stimulated B cells, could effectively inhibit T cell migration (FIG. 8). Moreover, the effects of conditioned supernatants were lost when Brefeldine A, which is an inhibitor of B cell secretory pathways, was used to inhibit the release of the peptide from B cells in to the conditioned medium, see (FIG. 8).

We have now definitively identified the secreted peptide released from B cells in response to adiponectin stimulation. Using mass spectrometric analysis adiponectin conditioned B cell supernatant, as well as the relevant control supernatants were purified and analysed by LC-MS/MS. Comparative analysis of a protein sequence database revealed a single candidate peptide unique to the adiponectin conditioned B cell supernatant, described in Table 1, below.

TABLE 1

Candidate peptide for the peptide reveled by comparative analysis of B cell supernatants

| m/z | Elution time (min) | Score | Modification | Association protein | Sequence |
|---|---|---|---|---|---|
| 774.88 | 13.2 | 63.1 | NA | 14-3-3 zeta/delta | SVTEQGAELSNEER (SEQ ID NO: 1) |

Due to the statistically stringent nature of the fragmentation analysis, the software was able to provide a definitive sequence with a high probability of accuracy and to identify the 14.3.3 zeta/delta (14.3.3.ζδ) protein as the precursor protein. Indeed the peptide represents amino acids 28-41 of the 14.3.3ζδ protein, which in turn is a 245 amino acid product of the YWHAZ gen. Stringent database searches demonstrate that the peptide sequence is unique to this protein and is not shared, even by the other six members of the 14.3.3 family of proteins (FIG. 9). The peptide is not a member of any known family of immuno-regulatory molecules and due to its chemistry, has attractive therapeutic potential.

Figure 10:
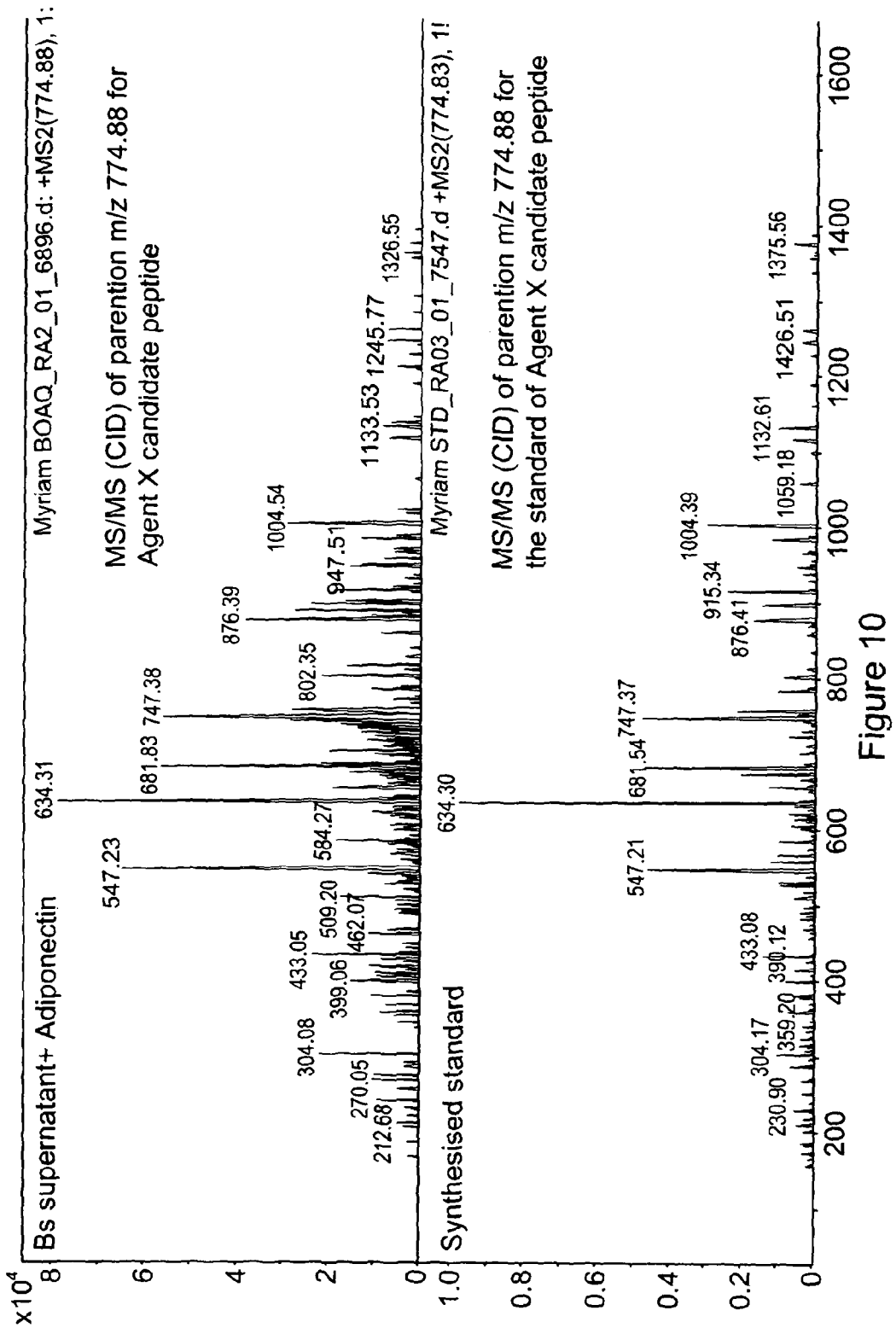
FIG. 10: Comparison of MS/MS parent ion m/z 774.88 from B cell supernatants and a synthetic version of the peptide.

We have been able to successfully synthesise the peptide. Comparative analysis of the B cell derived peptide and the synthetic version show identical mass:charge ratios in mass spectrometry analysis, showing that the native peptide has not been subject to post-translational modification prior to excision from the 14.3.3. zeta/delta protein and secretion from B cells (FIG. 10).

Figure 11A:
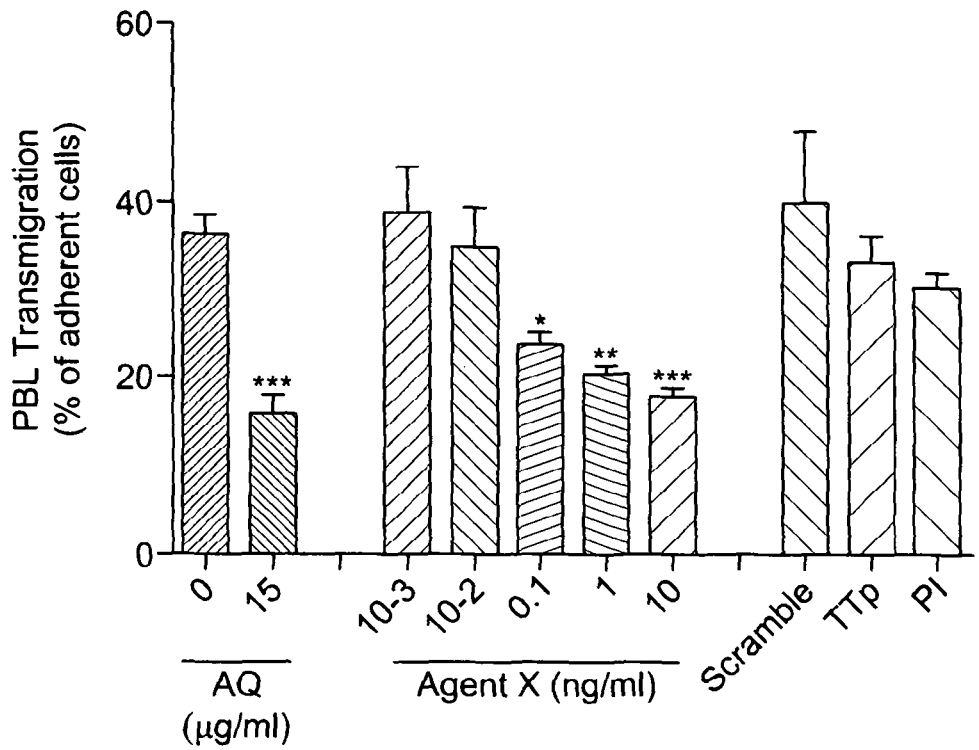
FIG. 11a is a graph of PBL transmigration for various samples.
Figure 11B:
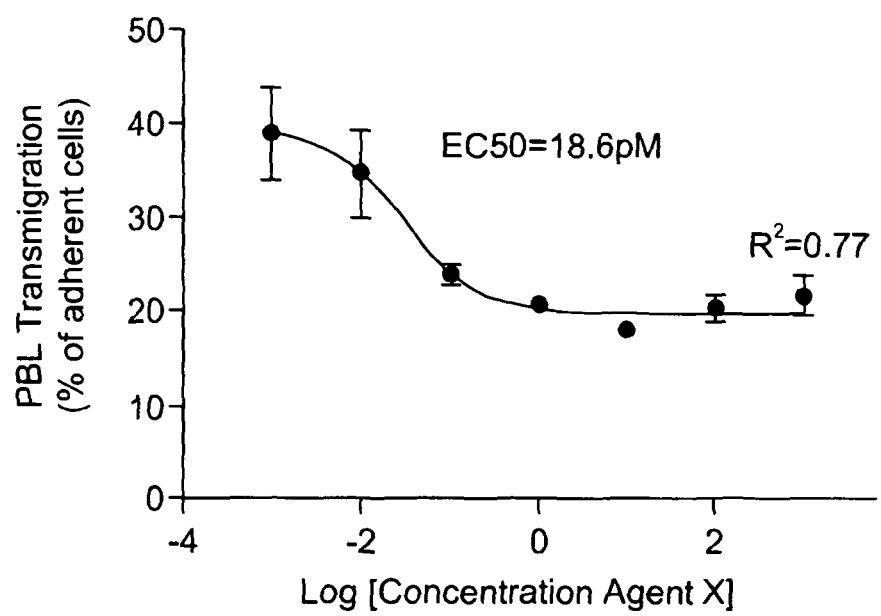
FIG. 11b is a graph showing PBL transmigration versus log concentration.
Figure 12:
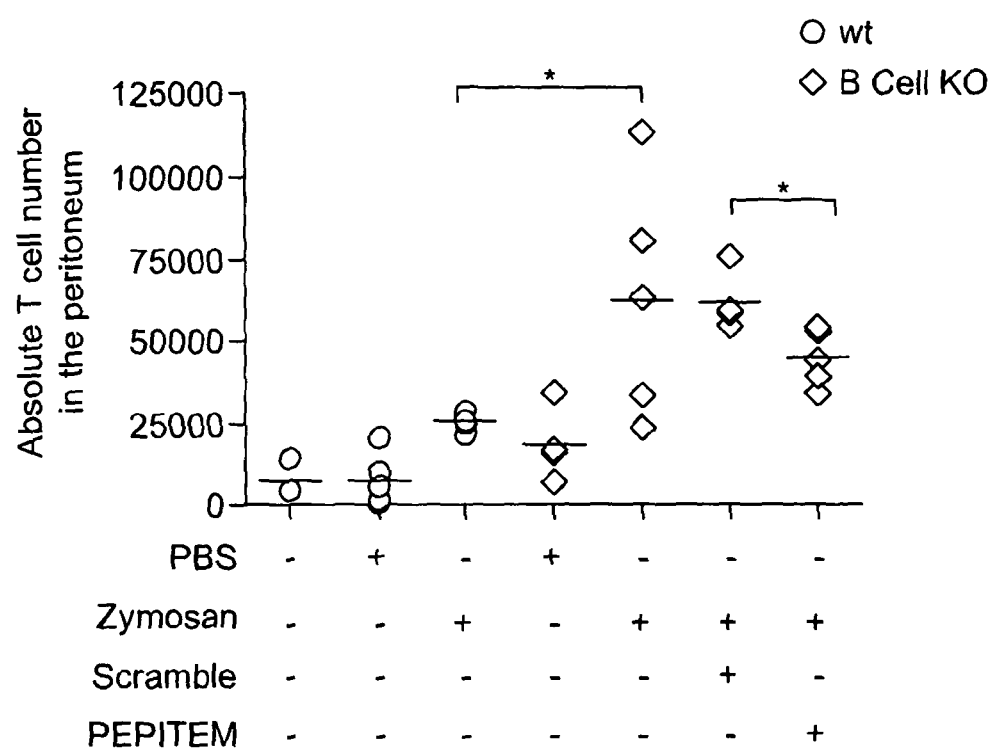
FIG. 12: Absolute number of T cells in the inflamed peritoneum of wild type or B cell knockout mice in the presence or absence of the peptide.
Figure 13A:
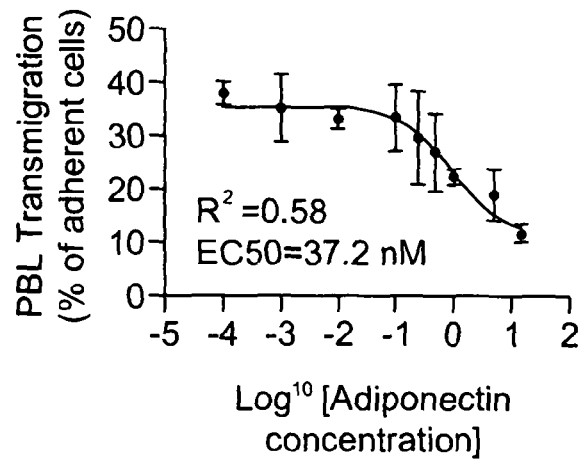
FIG. 13: The effect of adiponectin (Aq) on the transendothelial cell migration of peripheral blood lymphocytes.
  (A) Dose response with an EC50 of ≈40 nM conducted in static adhesion assay.
  (B) The effects of 15 μg/ml Aq on lymphocyte migration in a flow based assay (mimics the flow of blood).
  (C) The inhibitory pathway is effective on endothelial cells isolated form different tissues (HUVEC=Umbilical cord; HSAVEC=saphenous vein; HSEC=liver sinusoidal endothelial cells; HDMEC=Dermal microvascular endothelium).
  (D) The effects of an AMP-kinase inhibitor on the effects of adiponectin. AMPK is a signalling adapter that is required for adiponectin-receptor signalling.
Figure 13B:
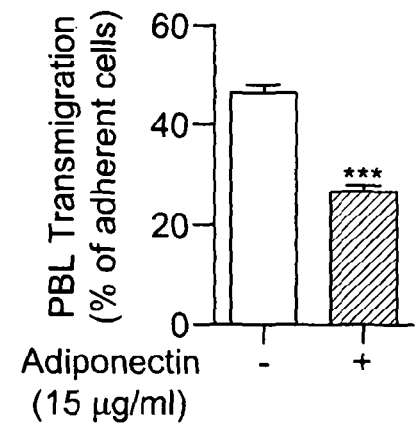
Figure 13C:
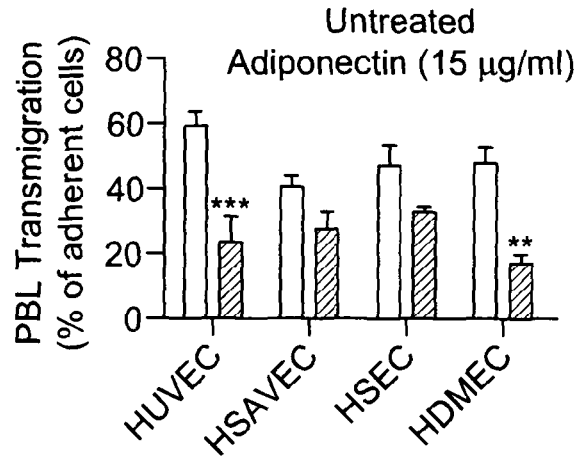
Figure 13D:
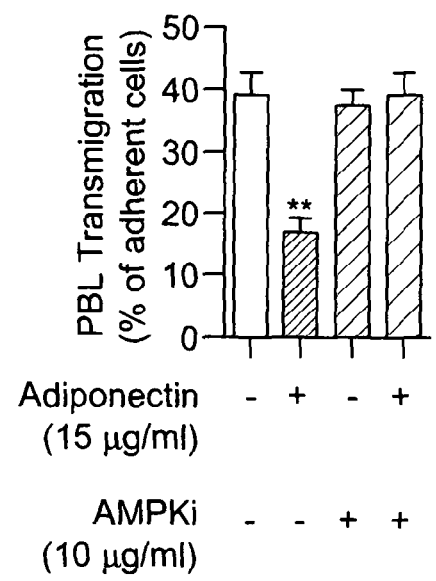

The peptide has efficacy both in vitro and in vivo. Using the synthetic peptide we constructed a dose response curve in our in vitro assay of T cell migration (FIG. 11). The peptide has an EC50 of ≈20 pM in this assay. We have also utilised the peptide in an in vivo model of acute, zymosan induced peritonitis (FIG. 12). In this model we first showed that the knockout of B lymphocytes (the cellular source of the peptide) resulted in an increase in the recruitment of T lymphocytes into the peritoneal cavity. We then conducted the experiment after injection of the peptide into the blood and peritoneum cavity of the B cell knockout mice. The peptide was able to significantly reduce the recruitment of T cells to the peritoneum after challenge with zymosan (FIG. 12).

Without being bound by theory, we understand that the following represents the paradigm by which PEPITEM regulates T cell trafficking across endothelial cells during inflammation: Adiponectin, operating through the receptors Adipo-R1 and Adipo-R2 (AR1/2), stimulates the release the immune-regulatory peptide, PEPITEM, from B cells, which are recruited to the endothelial cell surface during inflammation. PEPITEM stimulates endothelial cells through its cognate receptor, promoting the formation and release of sphingosine-1-phosphate (S1P). S1P in turn stimulates T cells recruited to the endothelial cell surface during Inflammation through the S1P-receptor(s) S1PR1/4, a signal that inhibits the ability of T cells to traffic across the endothelial cell barrier and enter inflamed tissue.

The following Examples present experimental proofs for the function of this pathway in both in vitro and in vivo studies, demonstrate changes in pathway function associated with chronic auto-immune disease in humans, and describe the identity the PEPITEM peptide.

Example 1

Adiponectin Inhibits the Transendothelial Cell Migration of Peripheral Blood Lymphocytes (PBL).

Endothelial cells were cultured in low serum medium and stimulated with TNF-α/IFN-γ for 24 hours in the absence of adiponectin. PBL were isolated and treated with adiponectin at 0.0001 to 15 µg/ml for one hour.

The results are shown in FIG. 1, where part (a) shows that PBL transmigration was significantly and dose dependently reduced by adiponectin in a static adhesion assay; part (b) shows that adiponectin had an EC50 of 0.94 µg/ml as determined by linear regression; and part (c) shows that Adiponectin was equally effective at inhibiting PBL migration in a flow based adhesion assay. Data is representative of at least three independent experiments and were analysed using t-test, one-way ANOVA and Dunnett's multiple comparisons post-test. *p≤0.01, p≤0.001, *p≤0.0001.

Inhibition of AMPK with Compound C Restores the Migration of PBL.

Endothelial cells were cultured in low serum medium and stimulated with TNF-α/IFN-γ for 24 hours. Compound C was added to PBL at 10 µg/ml for 30 minutes prior to addition of adiponectin at 15 µg/ml for 1 hour. Adiponectin treatment induced a decrease of transmigration, which was restored to normal, control levels in the presence of compound C. The results are shown in FIG. 2, where data is representative of three experiments and were analysed using one-way ANOVA and Dunnet's multiple comparisons post-test. p≤0.001, *p≤0.0001.

PBL from T1D Patients are Released from the Inhibitory Effect of Adiponectin on Transendothelial Cell Migration.

Endothelial cells were cultured in low serum medium and stimulated with TNF-α/IFN-γ for 24 hours in absence of adiponectin. The results are shown in FIG. 3. Part a) shows that Adiponectin-mediated inhibition of PBL transmigration is lost in T1D; and part b) shows that the percentage of inhibition was calculated by dividing the percentage of transmigration with adiponectin treatment by the percentage of transmigration of untreated PBL. n=13 for HC groups and n=12 for T1D group. Data was analysed using t-test and one-way ANOVA and Bonferonni's multiple comparisons post-test. ***p≤0.0001.

The Expression of Adiponectin Receptors on PBL is Reduced in Patients with T1D.

Figure 4A:
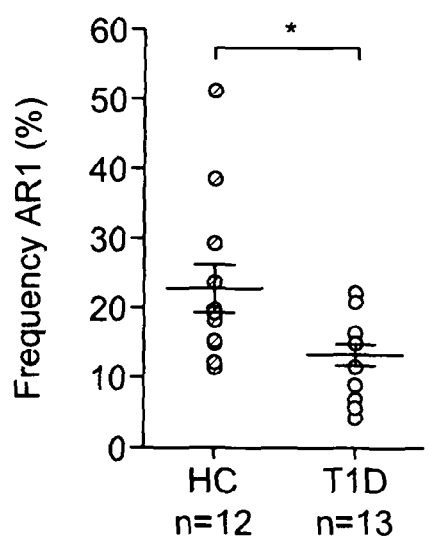
FIG. 4a is a graph showing frequency of PBL expressing adiponectin receptor AR1 in T1D and control samples.
Figure 4B:
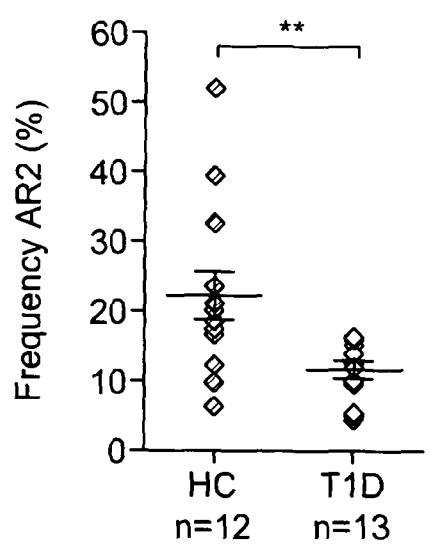
FIG. 4b is a graph showing frequency of PBL expressing adiponectin receptor AR2 in T1D and control samples.

The frequency of PBL expressing adiponectin receptors AR1 or AR2 were determined for each healthy or diseased subject and are shown in FIGS. 4a) and 4b), respectively. Data is represented as mean±SEM and was analysed using t-test or Mann Whitney t-test when data did not pass the Kolmogorov-Smirnov normality test.

The Expression of Adiponectin Receptors in T1D or Healthy Control Subjects Correlates with the Inhibition of Lymphocyte Migration by Adiponectin.

Figure 5A:
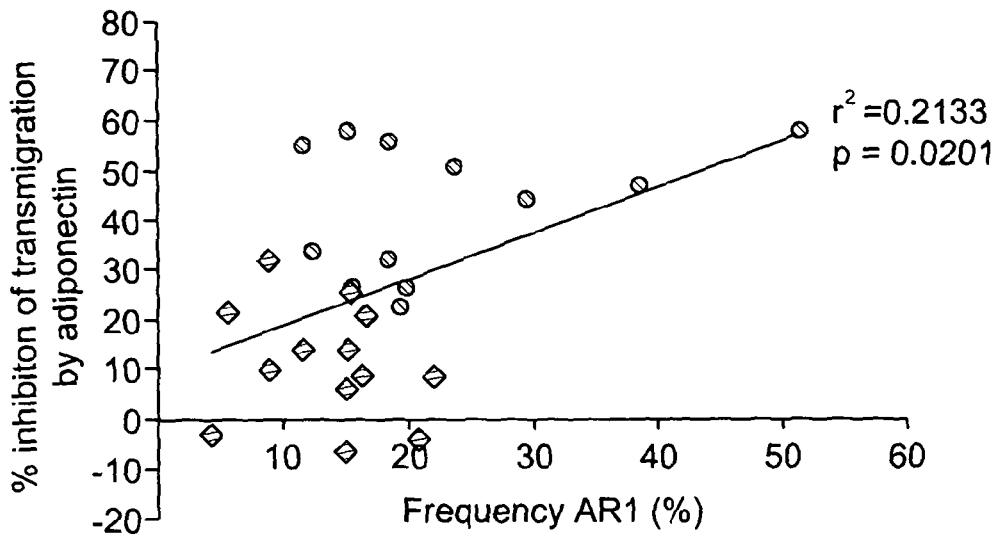
FIG. 5a is a graph of % inhibition of transmigration versus frequency of AR1 expression.
Figure 5B:
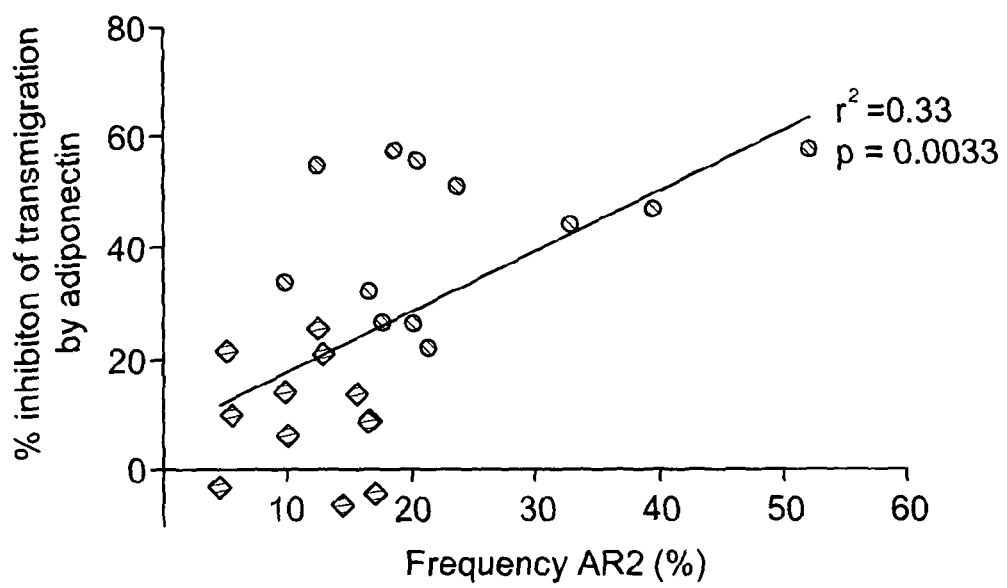
FIG. 5b is a graph of % inhibition of transmigration versus frequency of AR2 expression.

FIG. 5a) shows the correlation between the expression of AR1 and inhibition of lymphocyte migration, whilst FIG. 5b) shows the correlation between the expression of AR2 and inhibition of lymphocyte migration. Correlations were determined using linear regression analysis.

The Expression of Adiponectin Receptors on Different Leukocyte Subsets.

Figure 6A:
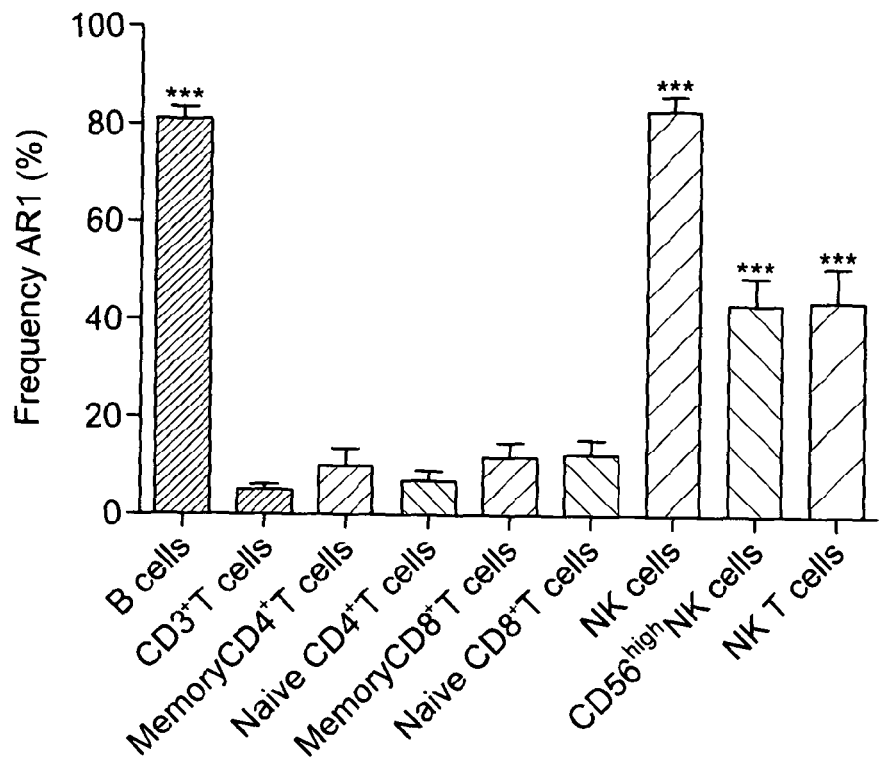
FIG. 6a is a graph showing frequency of AR1 expression for different cell types.
Figure 6B:
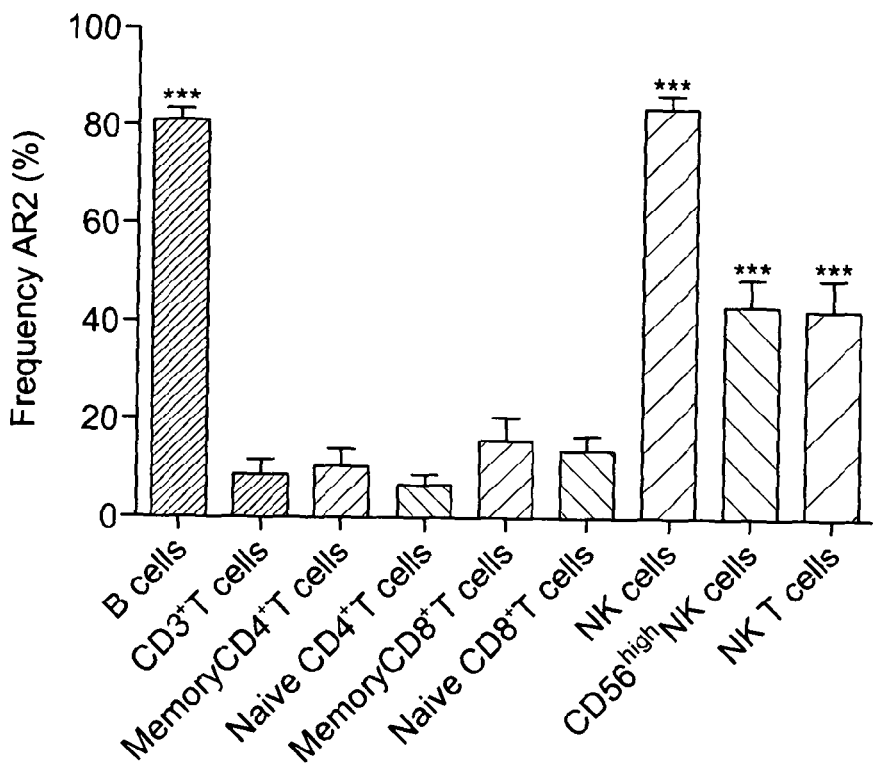
FIG. 6b is a graph showing frequency of AR2 expression for different cell types.

FIGS. 6a) and b) show the expression of AR1 (FIGS. 6a) and AR2 (FIG. 6b) on different cell types. Data is mean±SEM and are representative of seven healthy controls. Data was analysed using one-way ANOVA and Bonferroni's multiple comparisons post-hoc test. ***$p \le 0.0001$.

B Cells Mediate the Adiponectin-Induced Inhibition of T Cell Migration.

FIG. 7a) shows that the migration of PBL is lost when they are depleted of B cells (Bs) and regained when B cells are added back to isolated T cells. FIG. 7b) shows that the migration of natural killer cells is not affected by adiponectin and addition of NKs to T cells does not regulate the migration of the T cells. Data is mean±SEM and are representative of at least three independent experiments. Data was analysed using one-way ANOVA and Bonferroni's multiple comparisons post-test. $p \le 0.001$, *$p \le 0.0001$.

B Cells Modulate PBL Transmigration Through Secretion of a Peptide.

B cells were isolated and incubated in presence or absence of adiponectin at 15 µg/ml. Supernatant was taken after one hour and added to Bs-ve PBL which significantly restored the adiponectin inhibition of PBL transmigration. For some experiments, B cells were treated with Brefeldin A, an inhibitor of B cell secretion. These supernatants were not able to regulate the migration of T cells. This is shown in FIG. 8, where the data is shown as mean±SEM and is representative of three independent experiments analysed using one-way ANOVA and Bonferroni's multiple comparison post test. ***$p < 0.001$, ns=non significant.

The sequence of the peptide was determined and it is shown in FIG. 9 together with the different isoforms of the 14.3.3 proteins. See also Table 1 above.

Comparison of MS/MS Parent Ion m/z 774.88 from B Cell Supernatants and a Synthetic Version of the Peptide.

The ion m/z 774.88 is a fragmentation product of the analysis protocol and is generally only of use for identification using MS/MS, but can be an important parameter for comparison.

A comparison of the Mass Spec profiles of parent ion m/z 774.88 from B cell supernatants and a synthetic version of the peptide analysis is shown in FIG. 10, revealing identical mass:charge ratios. This confirmed sequence identity and showed that the peptide is not subject to post-translational modification prior to secretion.

The Peptide Inhibits T Cell Migration Across Endothelial Cells In Vitro.

PBL were treated with Adiponectin (15 µg/ml as positive control) or the peptide at concentrations between 0.001 and 10 ng/ml, a scramble peptide was used as a negative control (used 10 ng/ml). Other bioactive peptides were also used to demonstrate specificity of the peptide (i.e. tetanus toxoid peptide (TTp) at 10 ng/ml and pro-insulin (PI) at 10 ng/ml). The results are shown in FIG. 11. FIG. 11 a) shows that PBL transmigration was dose-dependently reduced in presence of the peptide but not in the presence of the scrambled peptide, TTp or PI controls. FIG. 11b) shows that the EC50 of the peptide (18.6 pM) was calculated using non linear regression analysis. Data is representative of three independent experiments and was analysed using one-way ANOVA and Bonferroni's multiple comparison post test. *$p \le 0.01$, $p \le 0.001$, *$p \le 0.0001$.

Absolute Number of T Cells in the Inflamed Peritoneum of Wild Type or B Cell Knockout Mice in the Presence or Absence of the Peptide.

Leukocytes were collected from the peritoneum after 48 hours injection of zymosan (or PBS as control) with or without the peptide or a scrambled peptide. T cells were identified by expression of CD3. The peptide or a scrambled peptide was injected at a final concentration of 300 µg/mouse. The results are shown in FIG. 12, where data for each group is the mean and was analysed using one-way ANOVA and Bonferroni's multiple comparisons post-test. *$p \le 0.01$.

Example 2

This Example shows the results of further work undertaken and thus compliments Example 1.

The Effect of Adiponectin (AQ) on the Transendothelial Cell Migration of Peripheral Blood Lymphocytes (PBL).

Refer to FIG. 13. Endothelial cells were cultured in low serum medium and stimulated with TNF-α/IFN-γ for 24 hours in the absence of adiponectin. PBL were isolated and treated with adiponectin at 0.0001 to 15 µg/ml for one hour. Part (a) shows that PBL transmigration was significantly and dose dependently reduced by adiponectin in a static adhesion assay and that adiponectin had an EC50 of ~40 nM as determined by linear regression; and part (b) shows that Adiponectin was equally effective at inhibiting PBL migration in a flow based adhesion assay; and part (c) shows that Adiponectin is effective on endothelial cells isolated from different tissues such as HUVEC (Umbilical cord), HSEC (liver sinusoidal endothelial cells) and DMEC (Dermal microvascular endothelium) but not HSAVEC (saphenous vein). In part (d), compound C, an AMP-kinase inhibitor, was added to PBL at 10 µg/ml for 30 minutes prior to addition of adiponectin at 15 µg/ml for 1 hour. AMPK is a signalling adapter that is required for adiponectin-receptor signalling. Adiponectin treatment induced a decrease of transmigration, which was restored to normal control levels in the presence of compound C. These data indicate that adiponectin has a strong capacity to regulate the transmigration of lymphocytes through action on its receptors expressed on PBL. Data is a pool of at least three independent experiments and were analysed using t-test, one-way ANOVA and Dunnett's multiple comparisons post-test.$p \le 0.01$, *$p \le 0.001$.

T Cells do not Posses Adiponectin Receptors.

The simplest interpretation of the previous experiment is that T cells are under the direct control of Aq. However, T cells lack the appropriate receptors. However, other leukocytes do have Adipo-R1/2 and both monocytes and B cells show high levels of expression.

Expression of both adiponectin receptors, AdipoR1 and AdipoR2, was measured on PBMC by flow cytometry using rabbit anti-human adiponectin receptor 1 and 2 antibodies (Phoenix peptides). Adiponectin receptor expression is shown on the horizontal axis against pan markers of PBMC sub-populations (vertical axis). AdipoR1 and AdipoR2 are highly expressed on monocytes (CD14+) and on B cells (CD19+) but at very low levels on T cells (CD3+). This indicates that adiponectin cannot directly control T cell migration.

B Cells are Required for the Adiponectin Mediated Inhibition of T Cell Trafficking.

Figure 14:
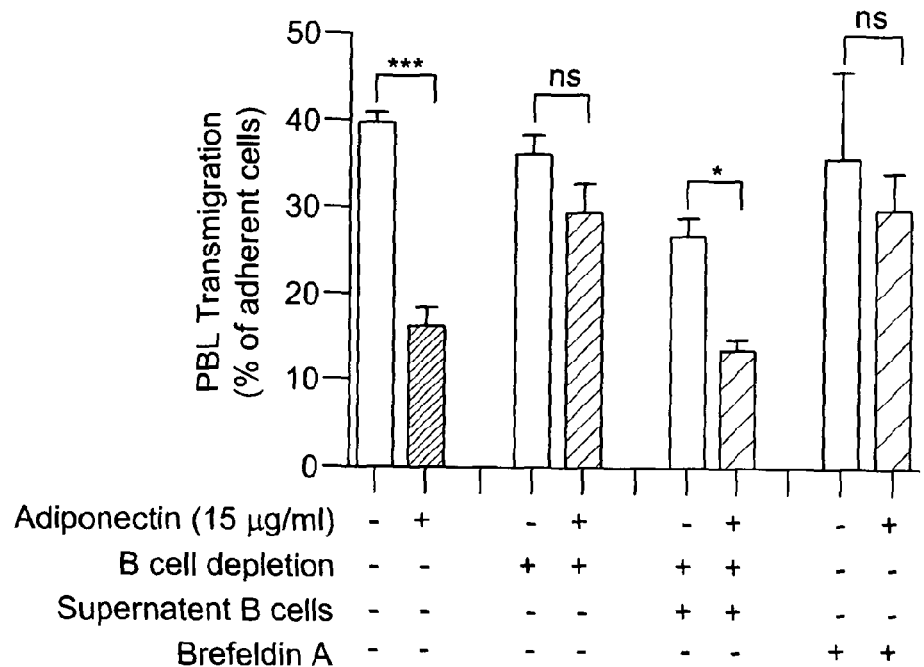
FIG. 14: B cells are required for the adiponectin mediated inhibition of T cell trafficking.

Refer to FIG. 14. Endothelial cells were cultured in low serum medium and stimulated with TNF-α/IFN-γ for 24 hours in the absence of adiponectin. PBL transmigration was measured after removal of B cells using bead positive selection and after reconstitution with B cells that were isolated using bead negative selection in presence or absence of adiponectin (15 μg/ml). Supernatants from adiponectin-treated B cells or B cell treated with Brefeldin A to block protein secretion were added to PBL.

Removing B cells form the peripheral blood lymphocyte preparation completely inhibited this response. This could be reconstituted using supernatants from Adiponectin stimulated B cells that could also effectively inhibit lymphocyte migration, but this effect was lost when supernatants were prepared in the presence of Brefeldin-A, an inhibitor of B cell secretion. These data demonstrate that a soluble mediator released form B cells is required.

Data is a pool at least three independent experiments and was analysed using one-way ANOVA and Bonferroni's multiple comparison post test. *p≤0.05, ***p≤0.001.

A 14 Amino Acid Peptide Released from B Cells Regulates T Cell Trafficking

Refer to FIG. 15. B cells were isolated using negative selection and incubated with adiponectin for an hour. Supernatants were recovered and purified on a C18 columns to remove large size proteins and acquired by mass spectrometry. The proteomic analysis using mass spectrometry of supernatants from AQ stimulated B cells revealed a 14 amino acid peptide with the sequence SVTEQGAELSNEER (SEQ ID NO: 1). Comparing this to an in silico library of published and predicted sequences, the peptide demonstrated exact sequence homology to a single human protein, and represents amino acids 28-41 of the 14.3.3 zeta/delta (14.3.3.ζδ) protein, which in turn is a 245 amino acid product of the YWHAZ gene. The peptide is not a member, nor is it related to, nor does it have sequence similarity to, any of the known families of immune-regulatory peptides. Analysis of synthetic peptide by mass spectrometry showed an identical mass:charge ratio to the native peptide (m/z=774.88), demonstrating that the B-cell derived product was not subject to any form of post translational modification prior to release. These data indicate that the 14 amino acid peptide identified is the mediator released by B cells under adiponectin stimulation.

PEPITEM Inhibits T Cells Transmigration

Refer to FIG. 16. Endothelial cells were cultured in low serum medium and stimulated with TNF-α/IFN-γ for 24 hours in the absence of adiponectin. PBL were treated with Adiponectin (15 μg/ml as positive control) or the peptide at concentrations between 0.001 and 10 ng/ml, a scramble peptide was used as a negative control (10 ng/ml). Other bioactive peptides were also used to demonstrate specificity of the peptide (i.e. tetanus toxoid peptide (TTp) at 10 ng/ml and pro-insulin (PI) at 10 ng/ml). Part (a) shows that PBL transmigration was dose-dependently reduced in presence of the peptide but not in the presence of the scrambled peptide, TTp or PI controls. Part (b) shows that the EC50 of the peptide (18.6 pM) was calculated using non linear regression analysis. The data indicates that PEPITEM is able to inhibit PBL transmigration similarly to adiponectin. Data is a pool of at least three independent experiments and was analysed using one-way ANOVA and Bonferroni's multiple comparison post test. *p≤0.05, p≤0.01, *p≤0.001.

PEPITEM Inhibits T Cell Migration AND Promotes the Recruitment of Anti-Inflammatory Regulatory T Cells Refer to FIG. 17. Endothelial cells were cultured in low serum medium and stimulated with TNF-α/IFN-γ for 24 hours in the absence of adiponectin. PBL and the different subsets and PEPITEM were added to different endothelial cells and transmigration was measured. The different subsets were isolated using negative selection for Treg, CD4+ and CD8+ memory and naïve T cells. Positive selection was used to isolate the different monocyte subsets.

Part (a) shows that PEPITEM inhibits T cell migration across EC with the same pattern as adiponectin on different endothelial cell type. Part (b) shows that PEPITEM is effective at inhibiting the transmigration of memory CD4+ and CD8+ T cells, but it has no effect neutrophils, or monocytes (including CD16– and CD16+ subsets. Naïve lymphocytes were not assessed in this analysis as they do not adhere to the endothelial cell monolayer. Part (c) shows the efficiency of the migration of regulatory T cells (Treg), which have anti-inflammatory functions, was increased by PEPITEM. These data indicate that PEPITEM is able to specifically modulate transmigration of memory T cells and Treg.

Data is a pool of at least three independent experiments and was analysed using t-test and one-way ANOVA and Bonferroni's multiple comparison post test. *p≤0.05, p≤0.01, *p≤0.001.

PEPITEM does not Directly Regulate T Cell Migration

Refer to FIG. 18. Endothelial cells were cultured in low serum medium and stimulated with TNF-α/IFN-γ for 24 hours in the absence of adiponectin. PEPITEM was added with the PBL on the endothelial cells or endothelial cells were pre-treated with PEPITEM and PBL added after washes or PBL were pre-treated with PEPITEM, washed and added to the endothelial cells.

When PBL were treated with PEPITEM and the agent was washed away prior to assay on endothelium, the efficiency of lymphocyte migration was not affected. However, pre-treating the endothelial cells with PEPITEM resulted in inhibition of lymphocyte trafficking. These data indicate that PEPITEM operates by stimulating endothelial cells to release an agent that inhibits T cell trafficking.

Data is a pool of three independent experiments and was analysed using paired t-test *p≤0.05, **p≤0.01.

The Induction of Sphingosine-1-Phosphate (S1P) Synthesis by Endothelial Cells Inhibits T Cell Migration.

Refer to FIG. 19. PBL or B cell depleted PBL transmigration across IFN-γ/TNF-α treated HUVEC was measured after blockade of S1P signalling using S1PR antagonist (W146, 10 μM) in presence or absence of (part a) adiponectin (15 μg/ml) or (part b) PEPITEM. B cell depleted PBL were pre-treated with S1P at different concentrations (0-100 μM) and transmigration across IFN-γ/TNF-α treated HUVEC was measured (part c). Levels of SPHK1 and SPHK2 mRNA expression determined by real-time PCR of RNA from B cells and HUVEC (part d, n=2). PBL transmigration was measured across IFN-γ/TNF-α treated HUVEC pre-treated with SPHK1 specific inhibitor (5 μM) in presence of PEPITEM (10 ng/ml) (part e).

The data shows that antagonism of the S1P receptor on T cells results in loss of adiponectin and PEPITEM inhibition on T cell transmigration (part a, b). Part (c) shows that addition of S1P to B cell depleted T cells restores the inhibition of transmigration; and part (d) shows high expression of S1P kinase 1 and 2 in HUVEC (SPHK1 and 2); and part (e) shows that inhibition of SPHK1 releases lymphocytes from the inhibitory effect of PEPITEM. These data indicates that PEPITEM stimulates endothelial cells to release S1P, which in turn inhibits lymphocyte transmigration.

Data is a pool of at least three independent experiments and was analysed using t-test and one-way ANOVA and Bonferroni's multiple comparison post test. *p≤0.05, p≤0.01, *p≤0.001.

S1P Regulates the Affinity of the Lymphocyte Integrin LFA-1.

Refer to FIG. 20. 96 well plates were coated with 50 ug/ml of recombinant ICAM overnight at 4° C. The plate was blocked using PBS 4% BSA for an hour at room temperature and PBL treated with IP-10 (10 ng/ml) and/or S1P (10 uM) were added for 30 minutes. Excess of unbound PBL was washed and PBL were labelled for the intermediate affinity site of the lymphocyte integrin LFA-1 (CD11a/CD18; αLβ2) using the KIM127 antibody (10 ug/ml) and for the high affinity site using antibody 24 (10 ug/ml) at 4° C. The expression of both affinity site was measured on memory T cells using mean fluorescence intensity (MFI). The data shows that the expression of both intermediate and high affinity sites increased upon IP-10 stimulation is down-regulated in presence of S1P. The data indicates that S1P regulate lymphocyte transmigration by modulating the affinity of the integrin LFA-1 that is essential to lymphocyte transmigration. Data is a pool of two independent experiments.

Absolute Number of T Cells in the Inflamed Peritoneum of Wild Type or B Cell Knockout Mice in the Presence or Absence of the Peptide.

Refer to FIG. 21. In part (a), wild-type or B cell knock-out (Jh-/-) BALB/c mice were injected with 100 ug zymosan. Leukocytes were collected from the peritoneum after 48 hours injection of zymosan (or PBS as control) with or without the peptide or a scrambled peptide. T cells were identified by expression of CD3. The peptide or a scrambled peptide was injected at a final concentration of 300 μg/mouse. The results are shown in part (a), where data for each group is the mean and was analysed using one-way ANOVA and Bonferroni's multiple comparisons post-test. *p≤0.01. In part (b), wild-type or B cell knock-out C56BL/6 mice were injected with *Salmonella typhirium*. After 5 days, liver were collected and sections stained for T cells. The data in part (b) shows the number of T cells per infection loci in liver sections.

The data shows that absence of B cells in mouse results in higher recruitment of T cells in the peritoneum upon zymosan-induced inflammation and *Salmonella* infection. This is reduced in the zymosan treated B cell knock-out mice by PEPITEM but not by the scrambled control. These data indicates that B cells are essential to regulate recruitment of T cells during inflammation in vivo by release of PEPITEM at sites of inflammation.

The Adiponectin/PEPITEM Pathway is Altered in Patients with Type 1 Diabetes

Refer to FIG. 22. The frequency of PBL expressing adiponectin receptors AR1 or AR2 were determined for each healthy or diseased subject by flow cytometry and are shown in part (a) and (b), respectively. Data is represented as mean±SEM and was analysed using t-test or Mann Whitney t-test when data did not pass the Kolmogorov-Smirnov normality test. Endothelial cells were cultured in low serum medium and stimulated with TNF-α/IFN-γ for 24 hours in the absence of adiponectin. PBL were isolated from healthy controls and patients with type 1 diabetes and treated with adiponectin 15 μg/ml for one hour. Part (c) shows a correlation between the expression of AdipoR2 and inhibition of lymphocyte migration, Correlations were determined using linear regression analysis. Part (d) shows the transmigration of PBL from newly diagnosed patient with type 1 diabetes, pre-treated with adiponectin or PEPITEM (n=5). Data was analysed using t-test **p<0.01.

The results show in part (a and b), lower expression of both adiponectin receptors (AdipoR1/2) on PBL from patients with type 1 diabetes; and part (b) shows that the lower expression of AdipoR2, the lower is the capacity of adiponectin to inhibit lymphocyte transmigration; and in part (d), PEPITEM was still able to inhibit lymphocyte transmigration.

The data indicates that lymphocytes from patients with type 1 diabetes are released from the inhibitory effects of adiponectin because they express lower adiponectin receptors and this can be restored by exogenous addition of PEPITEM.

The invention claimed is:

1. A method for treatment of a T-cell mediated autoimmune disease, comprising administering to a patient in need thereof:
   a peptide consisting of no more than 20 amino acids and comprising N'-SVTEQGAELSNEER-C' (SEQ ID NO: 1) or an analogue or variant thereof that inhibits T cell migration; or
   a chimeric or fusion protein comprising said peptide, wherein the disease is selected from the group consisting of diabetes mellitus (type 1), rheumatoid arthritis, Crohn's disease and uveitis.

2. The method according to claim 1, wherein the disease is diabetes mellitus (type 1).

3. The method according to claim 1, wherein the migration of the T cells is trans-endothelial across the endothelium of the pancreatic microvasculature separating the islet cells from the blood supply.

4. The method according to claim 1, wherein the T cells are auto-reactive T cells.

5. The method according to claim 4, wherein the peptide serves to inhibit the recruitment of auto-reactive T cells to the islets of the pancreas.

6. The method according to claim 1, wherein the peptide, analogue, variant, or chimeric or fusion protein thereof as defined in claim 1 is administered in the form of a pharmaceutically acceptable composition.

* * * * *

SEQUENCE LISTING

```
<160> NUMBER OF SEQ ID NOS: 10

<210> SEQ ID NO 1
<211> LENGTH: 14
<212> TYPE: PRT
<213> ORGANISM: Homo sapiens

<400> SEQUENCE: 1

Ser Val Thr Glu Gln Gly Ala Glu Leu Ser Asn Glu Glu Arg
1               5                   10

<210> SEQ ID NO 2
<211> LENGTH: 42
<212> TYPE: RNA
<213> ORGANISM: artificial
<220> FEATURE:
<223> OTHER INFORMATION: Coding sequence generated for SEQ ID NO: 1

<400> SEQUENCE: 2
aguguuacug aacaaggugc ugaguuaucu aaugaggaga ga                           42
```

<210> SEQ ID NO 3
<211> LENGTH: 42
<212> TYPE: RNA
<213> ORGANISM: artificial
<220> FEATURE:
<223> OTHER INFORMATION: Alternative coding sequence generated for SEQ
      ID NO: 1

<400> SEQUENCE: 3
agcgucaccg agcagggcgc cgaauugucc aacgaagaga gg                              42

<210> SEQ ID NO 4
<211> LENGTH: 246
<212> TYPE: PRT
<213> ORGANISM: Homo sapiens

<400> SEQUENCE: 4

Met Thr Met Asp Lys Ser Glu Leu Val Gln Lys Ala Lys Leu Ala Glu
1               5                   10                  15

Gln Ala Glu Arg Tyr Asp Asp Met Ala Ala Ala Met Lys Ala Val Thr
            20                  25                  30

Glu Gln Gly His Glu Leu Ser Asn Glu Glu Arg Asn Leu Leu Ser Val
        35                  40                  45

Ala Tyr Lys Asn Val Val Gly Ala Arg Arg Ser Ser Trp Arg Val Ile
    50                  55                  60

Ser Ser Ile Glu Gln Lys Thr Glu Arg Asn Glu Lys Lys Gln Gln Met
65                  70                  75                  80

Gly Lys Glu Tyr Arg Glu Lys Ile Glu Ala Glu Leu Gln Asp Ile Cys
                85                  90                  95

Asn Asp Val Leu Glu Leu Leu Asp Lys Tyr Leu Ile Pro Asn Ala Thr
            100                 105                 110

Gln Pro Glu Ser Lys Val Phe Tyr Leu Lys Met Lys Gly Asp Tyr Phe
        115                 120                 125

Arg Tyr Leu Ser Glu Val Ala Ser Gly Asp Asn Lys Gln Thr Thr Val
    130                 135                 140

Ser Asn Ser Gln Gln Ala Tyr Gln Glu Ala Phe Glu Ile Ser Lys Lys
145                 150                 155                 160

Glu Met Gln Pro Thr His Pro Ile Arg Leu Gly Leu Ala Leu Asn Phe
                165                 170                 175

Ser Val Phe Tyr Tyr Glu Ile Leu Asn Ser Pro Glu Lys Ala Cys Ser
            180                 185                 190

Leu Ala Lys Thr Ala Phe Asp Glu Ala Ile Ala Glu Leu Asp Thr Leu
        195                 200                 205

Asn Glu Glu Ser Tyr Lys Asp Ser Thr Leu Ile Met Gln Leu Leu Arg
    210                 215                 220

Asp Asn Leu Thr Leu Trp Thr Ser Glu Asn Gln Gly Asp Glu Gly Asp
225                 230                 235                 240

Ala Gly Glu Gly Glu Asn
                245

<210> SEQ ID NO 5
<211> LENGTH: 255
<212> TYPE: PRT
<213> ORGANISM: Homo sapiens

```
<400> SEQUENCE: 5

Met Asp Asp Arg Glu Asp Leu Val Tyr Gln Ala Lys Leu Ala Glu Gln
1               5                   10                  15

Ala Glu Arg Tyr Asp Glu Met Val Glu Ser Met Lys Lys Val Ala Gly
            20                  25                  30

Met Asp Val Glu Leu Thr Val Glu Glu Arg Asn Leu Leu Ser Val Ala
        35                  40                  45

Tyr Lys Asn Val Ile Gly Ala Arg Arg Ala Ser Trp Arg Ile Ile Ser
    50                  55                  60

Ser Ile Glu Gln Lys Glu Glu Asn Lys Gly Gly Glu Asp Lys Leu Lys
65                  70                  75                  80

Met Ile Arg Glu Tyr Arg Gln Met Val Glu Thr Glu Leu Lys Leu Ile
                85                  90                  95

Cys Cys Asp Ile Leu Asp Val Leu Asp Lys His Leu Ile Pro Ala Ala
            100                 105                 110

Asn Thr Gly Glu Ser Lys Val Phe Tyr Tyr Lys Met Lys Gly Asp Tyr
        115                 120                 125

His Arg Tyr Leu Ala Glu Phe Ala Thr Gly Asn Asp Arg Lys Glu Ala
    130                 135                 140

Ala Glu Asn Ser Leu Val Ala Tyr Lys Ala Ala Ser Asp Ile Ala Met
145                 150                 155                 160

Thr Glu Leu Pro Pro Thr His Pro Ile Arg Leu Gly Leu Ala Leu Asn
                165                 170                 175

Phe Ser Val Phe Tyr Tyr Glu Ile Leu Asn Ser Pro Asp Arg Ala Cys
            180                 185                 190

Arg Leu Ala Lys Ala Ala Phe Asp Asp Ala Ile Ala Glu Leu Asp Thr
        195                 200                 205

Leu Ser Glu Glu Ser Tyr Lys Asp Ser Thr Leu Ile Met Gln Leu Leu
    210                 215                 220

Arg Asp Asn Leu Thr Leu Trp Thr Ser Asp Met Gln Gly Asp Gly Glu
225                 230                 235                 240

Glu Gln Asn Lys Glu Ala Leu Gln Asp Val Glu Asp Glu Asn Gln
                245                 250                 255

<210> SEQ ID NO 6
<211> LENGTH: 246
<212> TYPE: PRT
<213> ORGANISM: Homo sapiens

<400> SEQUENCE: 6

Met Gly Asp Arg Glu Gln Leu Leu Gln Arg Ala Arg Leu Ala Glu Gln
1               5                   10                  15

Ala Glu Arg Tyr Asp Asp Met Ala Ser Ala Met Lys Ala Val Thr Glu
            20                  25                  30

Leu Asn Glu Pro Leu Ser Asn Glu Asp Arg Asn Leu Leu Ser Val Ala
        35                  40                  45

Tyr Lys Asn Val Val Gly Ala Arg Arg Ser Ser Trp Arg Val Ile Ser
    50                  55                  60

Ser Ile Glu Gln Lys Thr Met Ala Asp Gly Asn Glu Lys Lys Leu Glu
65                  70                  75                  80

Lys Val Lys Ala Tyr Arg Glu Lys Ile Glu Lys Glu Leu Glu Thr Val
                85                  90                  95

Cys Asn Asp Val Leu Ser Leu Leu Asp Lys Phe Leu Ile Lys Asn Cys
            100                 105                 110
```

```
Asn Asp Phe Gln Tyr Glu Ser Lys Val Phe Tyr Leu Lys Met Lys Gly
            115                 120                 125

Asp Tyr Tyr Arg Tyr Leu Ala Glu Val Ala Ser Gly Glu Lys Lys Asn
        130                 135                 140

Ser Val Glu Ala Ser Glu Ala Ala Tyr Lys Glu Ala Phe Glu Ile
145                 150                 155                 160

Ser Lys Glu Gln Met Gln Pro Thr His Pro Ile Arg Leu Gly Leu Ala
                165                 170                 175

Leu Asn Phe Ser Val Phe Tyr Tyr Glu Ile Gln Asn Ala Pro Glu Gln
                180                 185                 190

Ala Cys Leu Leu Ala Lys Gln Ala Phe Asp Asp Ala Ile Ala Glu Leu
                195                 200                 205

Asp Thr Leu Asn Glu Asp Ser Tyr Lys Asp Ser Thr Leu Ile Met Gln
                210                 215                 220

Leu Leu Arg Asp Asn Leu Thr Leu Trp Thr Ser Asp Gln Gln Asp Glu
225                 230                 235                 240

Glu Ala Gly Glu Gly Asn
                245

<210> SEQ ID NO 7
<211> LENGTH: 247
<212> TYPE: PRT
<213> ORGANISM: Homo sapiens

<400> SEQUENCE: 7

Met Val Asp Arg Glu Gln Leu Val Gln Lys Ala Arg Leu Ala Glu Gln
1               5                   10                  15

Ala Glu Arg Tyr Asp Asp Met Ala Ala Ala Met Lys Asn Val Thr Glu
                20                  25                  30

Leu Asn Glu Pro Leu Ser Asn Glu Glu Arg Asn Leu Leu Ser Val Ala
                35                  40                  45

Tyr Lys Asn Val Val Gly Ala Arg Arg Ser Ser Trp Arg Val Ile Ser
        50                  55                  60

Ser Ile Glu Gln Lys Thr Ser Ala Asp Gly Asn Glu Lys Lys Ile Glu
65                  70                  75                  80

Met Val Arg Ala Tyr Arg Glu Lys Ile Glu Lys Glu Leu Glu Ala Val
                85                  90                  95

Cys Gln Asp Val Leu Ser Leu Leu Asp Asn Tyr Leu Ile Lys Asn Cys
                100                 105                 110

Ser Glu Thr Gln Tyr Glu Ser Lys Val Phe Tyr Leu Lys Met Lys Gly
            115                 120                 125

Asp Tyr Tyr Arg Tyr Leu Ala Glu Val Ala Thr Gly Glu Lys Arg Ala
        130                 135                 140

Thr Val Val Glu Ser Ser Glu Lys Ala Tyr Ser Glu Ala His Glu Ile
145                 150                 155                 160

Ser Lys Glu His Met Gln Pro Thr His Pro Ile Arg Leu Gly Leu Ala
                165                 170                 175

Leu Asn Tyr Ser Val Phe Tyr Tyr Glu Ile Gln Asn Ala Pro Glu Gln
                180                 185                 190

Ala Cys His Leu Ala Lys Thr Ala Phe Asp Asp Ala Ile Ala Glu Leu
                195                 200                 205

Asp Thr Leu Asn Glu Asp Ser Tyr Lys Asp Ser Thr Leu Ile Met Gln
                210                 215                 220
```

Leu Leu Arg Asp Asn Leu Thr Leu Trp Thr Ser Asp Gln Gln Asp
225                 230                 235                 240

Asp Gly Gly Glu Gly Asn Asn
                245

<210> SEQ ID NO 8
<211> LENGTH: 248
<212> TYPE: PRT
<213> ORGANISM: Homo sapiens

<400> SEQUENCE: 8

Met Glu Arg Ala Ser Leu Ile Gln Lys Ala Lys Leu Ala Glu Gln Ala
1               5                   10                  15

Glu Arg Tyr Glu Asp Met Ala Ala Phe Met Lys Gly Ala Val Glu Lys
            20                  25                  30

Gly Glu Glu Leu Ser Cys Glu Glu Arg Asn Leu Leu Ser Val Ala Tyr
        35                  40                  45

Lys Asn Val Val Gly Gly Gln Arg Ala Ala Trp Arg Val Leu Ser Ser
    50                  55                  60

Ile Glu Gln Lys Ser Asn Glu Glu Gly Ser Glu Glu Lys Gly Pro Glu
65                  70                  75                  80

Val Arg Glu Tyr Arg Glu Lys Val Glu Thr Glu Leu Gln Gly Val Cys
                85                  90                  95

Asp Thr Val Leu Gly Leu Leu Asp Ser His Leu Ile Lys Glu Ala Gly
            100                 105                 110

Asp Ala Glu Ser Arg Val Phe Tyr Leu Lys Met Lys Gly Asp Tyr Tyr
        115                 120                 125

Arg Tyr Leu Ala Glu Val Ala Thr Gly Asp Asp Lys Lys Arg Ile Ile
    130                 135                 140

Asp Ser Ala Arg Ser Ala Tyr Gln Glu Ala Met Asp Ile Ser Lys Lys
145                 150                 155                 160

Glu Met Pro Pro Thr Asn Pro Ile Arg Leu Gly Leu Ala Leu Asn Phe
                165                 170                 175

Ser Val Phe His Tyr Glu Ile Ala Asn Ser Pro Glu Glu Ala Ile Ser
            180                 185                 190

Leu Ala Lys Thr Thr Phe Asp Glu Ala Met Ala Asp Leu His Thr Leu
        195                 200                 205

Ser Glu Asp Ser Tyr Lys Asp Ser Thr Leu Ile Met Gln Leu Leu Arg
    210                 215                 220

Asp Asn Leu Thr Leu Trp Thr Ala Asp Asn Ala Gly Glu Glu Gly Gly
225                 230                 235                 240

Glu Ala Pro Gln Glu Pro Gln Ser
                245

<210> SEQ ID NO 9
<211> LENGTH: 245
<212> TYPE: PRT
<213> ORGANISM: Homo sapiens

<400> SEQUENCE: 9

Met Glu Lys Thr Glu Leu Ile Gln Lys Ala Lys Leu Ala Glu Gln Ala
1               5                   10                  15

Glu Arg Tyr Asp Asp Met Ala Thr Cys Met Lys Ala Val Thr Glu Gln
            20                  25                  30

Gly Ala Glu Leu Ser Asn Glu Glu Arg Asn Leu Leu Ser Val Ala Tyr
        35                  40                  45

```
Lys Asn Val Val Gly Gly Arg Arg Ser Ala Trp Arg Val Ile Ser Ser
 50                  55                  60

Ile Glu Gln Lys Thr Asp Thr Ser Asp Lys Lys Leu Gln Leu Ile Lys
 65                  70                  75                  80

Asp Tyr Arg Glu Lys Val Glu Ser Glu Leu Arg Ser Ile Cys Thr Thr
                 85                  90                  95

Val Leu Glu Leu Leu Asp Lys Tyr Leu Ile Ala Asn Ala Thr Asn Pro
            100                 105                 110

Glu Ser Lys Val Phe Tyr Leu Lys Met Lys Gly Asp Tyr Phe Arg Tyr
        115                 120                 125

Leu Ala Glu Val Ala Cys Gly Asp Asp Arg Lys Gln Thr Ile Asp Asn
130                 135                 140

Ser Gln Gly Ala Tyr Gln Glu Ala Phe Asp Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Asn Pro Glu Leu Ala Cys Thr Leu Ala
            180                 185                 190

Lys Thr Ala Phe Asp Glu Ala Ile Ala Glu Leu Asp Thr Leu Asn Glu
        195                 200                 205

Asp Ser Tyr Lys Asp Ser Thr Leu Ile Met Gln Leu Leu Arg Asp Asn
210                 215                 220

Leu Thr Leu Trp Thr Ser Asp Ser Ala Gly Glu Glu Cys Asp Ala Ala
225                 230                 235                 240

Glu Gly Ala Glu Asn
                245

<210> SEQ ID NO 10
<211> LENGTH: 245
<212> TYPE: PRT
<213> ORGANISM: Homo sapiens

<400> SEQUENCE: 10

Met Asp Lys Asn Glu Leu Val Gln Lys Ala Lys Leu Ala Glu Gln Ala
 1               5                  10                  15

Glu Arg Tyr Asp Asp Met Ala Ala Cys Met Lys Ser Val Thr Glu Gln
                 20                  25                  30

Gly Ala Glu Leu Ser Asn Glu Glu Arg Asn Leu Leu Ser Val Ala Tyr
            35                  40                  45

Lys Asn Val Val Gly Ala Arg Arg Ser Ser Trp Arg Val Val Ser Ser
 50                  55                  60

Ile Glu Gln Lys Thr Glu Gly Ala Glu Lys Lys Gln Gln Met Ala Arg
 65                  70                  75                  80

Glu Tyr Arg Glu Lys Ile Glu Thr Glu Leu Arg Asp Ile Cys Asn Asp
                 85                  90                  95

Val Leu Ser Leu Leu Glu Lys Phe Leu Ile Pro Asn Ala Ser Gln Ala
            100                 105                 110

Glu Ser Lys Val Phe Tyr Leu Lys Met Lys Gly Asp Tyr Tyr Arg Tyr
        115                 120                 125

Leu Ala Glu Val Ala Ala Gly Asp Asp Lys Lys Gly Ile Val Asp Gln
130                 135                 140

Ser Gln Gln Ala Tyr Gln Glu Ala Phe Glu Ile Ser Lys Lys Glu Met
145                 150                 155                 160

Gln Pro Thr His Pro Ile Arg Leu Gly Leu Ala Leu Asn Phe Ser Val
                165                 170                 175
```

```
Phe Tyr Tyr Glu Ile Leu Asn Ser Pro Glu Lys Ala Cys Ser Leu Ala
            180             185             190

Lys Thr Ala Phe Asp Glu Ala Ile Ala Glu Leu Asp Thr Leu Ser Glu
        195             200             205

Glu Ser Tyr Lys Asp Ser Thr Leu Ile Met Gln Leu Leu Arg Asp Asn
        210             215             220

Leu Thr Leu Trp Thr Ser Asp Thr Gln Gly Asp Glu Ala Glu Ala Gly
225             230             235             240

Glu Gly Gly Glu Asn
            245
```